United States Patent
George et al.

(10) Patent No.: US 8,956,398 B2
(45) Date of Patent: Feb. 17, 2015

(54) CUSTOM LENGTH STENT APPARATUS

(75) Inventors: Robert George, San Jose, CA (US);
David W. Snow, San Carlos, CA (US);
Harold F. Carrison, Pleasanton, CA (US); Pablo Acosta, Newark, CA (US)

(73) Assignee: J.W. Medical Systems Ltd., Weihai Shandong (CN)

( * ) Notice: Subject to any disclaimer, the term of this patent is extended or adjusted under 35 U.S.C. 154(b) by 252 days.

(21) Appl. No.: 13/015,389

(22) Filed: Jan. 27, 2011

(65) Prior Publication Data

US 2011/0125248 A1 May 26, 2011

Related U.S. Application Data

(60) Division of application No. 11/469,773, filed on Sep. 1, 2006, now Pat. No. 7,892,273, which is a continuation-in-part of application No. 10/412,714, filed on Apr. 10, 2003, now Pat. No. 7,137,993, which (Continued)

(51) Int. Cl.
*A61F 2/06* (2013.01)
*H04B 10/2575* (2013.01)
(Continued)

(52) U.S. Cl.
CPC .............. *H04B 10/2575* (2013.01); *A61F 2/91* (2013.01); *A61F 2/915* (2013.01); *A61F 2/95* (2013.01);
(Continued)

(58) Field of Classification Search
CPC .............. A61F 2/82; A61F 2/91; A61F 2/915; A61F 2002/826; A61F 2/95; A61F 2/0095; A61F 2/958; A61F 2002/9583; A61F 2002/828

USPC .............................. 623/1.11, 1.12, 1.16, 1.23
See application file for complete search history.

(56) References Cited

U.S. PATENT DOCUMENTS

| | | |
|---|---|---|
| 4,069,825 A | 1/1978 | Akiyama |
| 4,468,224 A | 8/1984 | Enzmann et al. |

(Continued)

FOREIGN PATENT DOCUMENTS

| | | |
|---|---|---|
| CN | 1856280 A | 11/2006 |
| DE | 1 953 1659 | 3/1997 |

(Continued)

OTHER PUBLICATIONS

Chu et al., "Preparation of Thermo-Responsive Core-Shell Microcapsules with a Porous Membrane and Poly(N-isopropylacrylamide) Gates," J Membrane Sci, Oct. 15, 2001; 192(1-2):27-39.

(Continued)

*Primary Examiner* — Katherine Dowe
(74) *Attorney, Agent, or Firm* — Kilpatrick Townsend & Stockton LLP

(57) ABSTRACT

Apparatus and methods for delivering prosthetic segments to a body lumen, utilize a device having an elongated flexible member including proximal and distal ends, a plurality of prosthetic segments releasably arranged axially along the elongated flexible member near the distal end and an outer sheath slidably disposed over at least a portion of the prosthetic segments. The apparatus further includes a separator disposed on the outer sheath and adapted to engage the prosthetic segments. The separator is also adapted to be retracted proximally over the prosthetic segments and advanced distally to separate a proximal group of the prosthetic segments from a distal group of the prosthetic segments which are to be deployed in the body lumen.

28 Claims, 22 Drawing Sheets

Related U.S. Application Data is a continuation-in-part of application No. 10/306,813, filed on Nov. 27, 2002, now abandoned.

(60) Provisional application No. 60/336,967, filed on Dec. 3, 2001, provisional application No. 60/364,389, filed on Mar. 13, 2002.

(51) Int. Cl.

| | | |
|---|---|---|
| *A61F 2/91* | (2013.01) | |
| *A61F 2/915* | (2013.01) | |
| *A61F 2/95* | (2013.01) | |
| *A61F 2/958* | (2013.01) | |
| *H01Q 3/26* | (2006.01) | |
| *A61F 2/00* | (2006.01) | |
| *A61F 2/82* | (2013.01) | |

(52) U.S. Cl.
CPC .............. *A61F 2/958* (2013.01); *H01Q 3/2676* (2013.01); *A61F 2/0095* (2013.01); *A61F 2002/826* (2013.01); *A61F 2002/828* (2013.01); *A61F 2002/91508* (2013.01); *A61F 2002/91533* (2013.01); *A61F 2002/9583* (2013.01); *A61F 2210/0033* (2013.01); *A61F 2210/0042* (2013.01)
USPC ........................ 623/1.12; 623/1.16

(56) References Cited

U.S. PATENT DOCUMENTS

| | | |
|---|---|---|
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | McGreevy et al. |
| 4,733,665 A | 3/1988 | Palmaz |
| 4,739,762 A | 4/1988 | Palmaz |
| 4,748,982 A | 6/1988 | Horzewski et al. |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |
| 4,891,225 A | 1/1990 | Langer et al. |
| 4,950,227 A | 8/1990 | Savin et al. |
| 4,988,356 A | 1/1991 | Crittenden et al. |
| 4,994,066 A | 2/1991 | Voss |
| 4,994,069 A | 2/1991 | Ritchart et al. |
| 4,994,298 A | 2/1991 | Yasuda |
| 5,013,318 A | 5/1991 | Spranza, III |
| 5,035,706 A | 7/1991 | Giantureo et al. |
| 5,040,548 A | 8/1991 | Yock |
| 5,061,273 A | 10/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,158,548 A | 10/1992 | Lau et al. |
| 5,192,297 A | 3/1993 | Hull |
| 5,195,984 A | 3/1993 | Schatz |
| 5,201,757 A | 4/1993 | Heyn et al. |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,261,887 A | 11/1993 | Walker |
| 5,273,536 A | 12/1993 | Savas |
| 5,282,823 A | 2/1994 | Schwartz et al. |
| 5,282,824 A | 2/1994 | Gianturco |
| 5,300,085 A | 4/1994 | Yock |
| 5,312,415 A | 5/1994 | Palermo |
| 5,328,469 A | 7/1994 | Coletti |
| 5,334,187 A | 8/1994 | Fischell et al. |
| 5,391,172 A | 2/1995 | Williams et al. |
| 5,421,955 A | 6/1995 | Lau et al. |
| 5,443,498 A | 8/1995 | Fontaine |
| 5,445,646 A | 8/1995 | Euteneuer et al. |
| 5,456,713 A | 10/1995 | Chuter |
| 5,458,615 A | 10/1995 | Klemm et al. |
| 5,470,315 A | 11/1995 | Adams |
| 5,478,349 A | 12/1995 | Nicholas |
| 5,484,444 A | 1/1996 | Braunschweiler et al. |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,522,882 A | 6/1996 | Gaterud et al. |
| 5,527,354 A | 6/1996 | Fontaine et al. |
| 5,531,735 A | 7/1996 | Thompson |
| 5,533,968 A | 7/1996 | Muni et al. |
| 5,534,007 A | 7/1996 | St. Germain et al. |
| 5,545,209 A | 8/1996 | Roberts et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,591,195 A | 1/1997 | Taheri et al. |
| 5,593,412 A | 1/1997 | Martinez et al. |
| 5,607,444 A | 3/1997 | Lam |
| 5,607,463 A | 3/1997 | Schwartz et al. |
| 5,628,755 A | 5/1997 | Heller et al. |
| 5,628,775 A | 5/1997 | Jackson et al. |
| 5,634,928 A | 6/1997 | Fischell et al. |
| 5,639,274 A | 6/1997 | Fischell et al. |
| 5,662,675 A | 9/1997 | Polanskyj Stockert et al. |
| 5,662,703 A | 9/1997 | Yurek et al. |
| 5,670,161 A | 9/1997 | Healy et al. |
| 5,676,654 A | 10/1997 | Ellis et al. |
| 5,683,451 A | 11/1997 | Lenker et al. |
| 5,690,644 A | 11/1997 | Yurek et al. |
| 5,693,085 A | 12/1997 | Buirge et al. |
| 5,697,948 A | 12/1997 | Marin et al. |
| 5,697,971 A | 12/1997 | Fischell et al. |
| 5,702,418 A | 12/1997 | Ravenscroft |
| 5,702,419 A | 12/1997 | Berry et al. |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,741,323 A | 4/1998 | Pathak et al. |
| 5,749,848 A | 5/1998 | Jang et al. |
| 5,749,890 A | 5/1998 | Shaknovich |
| 5,749,921 A | 5/1998 | Lenker et al. |
| 5,755,697 A | 5/1998 | Jones et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,792,144 A | 8/1998 | Fischell et al. |
| 5,797,951 A | 8/1998 | Mueller |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,090 A * | 12/1998 | Schuetz ...................... 623/1.11 |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |

(56) References Cited

U.S. PATENT DOCUMENTS

| | | |
|---|---|---|
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,921,971 A | 7/1999 | Agro et al. |
| 5,922,020 A | 7/1999 | Klein et al. |
| 5,941,869 A | 8/1999 | Patterson et al. |
| 5,951,585 A | 9/1999 | Cathcart et al. |
| 5,961,536 A | 10/1999 | Mickley et al. |
| 5,965,879 A | 10/1999 | Leviton |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 5,989,280 A | 11/1999 | Euteneuer et al. |
| 5,993,484 A | 11/1999 | Shmulewitz |
| 5,997,563 A | 12/1999 | Kretzers et al. |
| 6,004,328 A | 12/1999 | Solar |
| 6,007,517 A | 12/1999 | Anderson |
| 6,010,530 A | 1/2000 | Goicoechea |
| 6,022,359 A | 2/2000 | Frantzen |
| 6,022,374 A | 2/2000 | Imran |
| 6,027,519 A | 2/2000 | Stanford |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,050,999 A * | 4/2000 | Paraschac et al. ............ 606/107 |
| 6,056,722 A | 5/2000 | Jayaraman |
| 6,063,111 A | 5/2000 | Hieshima et al. |
| 6,066,155 A | 5/2000 | Amann et al. |
| 6,068,655 A | 5/2000 | Seguin et al. |
| 6,070,589 A | 6/2000 | Keith et al. |
| 6,090,063 A | 7/2000 | Makower et al. |
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,477 A | 9/2000 | Campbell et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler et al. |
| 6,132,460 A | 10/2000 | Thompson |
| 6,139,572 A | 10/2000 | Campbell et al. |
| 6,143,016 A | 11/2000 | Bleam et al. |
| 6,165,167 A | 12/2000 | Delaloye |
| 6,165,210 A | 12/2000 | Lau et al. |
| 6,171,334 B1 | 1/2001 | Cox |
| 6,179,878 B1 | 1/2001 | Duerig |
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,217,585 B1 | 4/2001 | Houser et al. |
| 6,238,991 B1 | 5/2001 | Suzuki |
| 6,241,691 B1 | 6/2001 | Ferrera et al. |
| 6,241,758 B1 | 6/2001 | Cox |
| 6,248,122 B1 | 6/2001 | Klumb et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,264,688 B1 | 7/2001 | Herklotz et al. |
| 6,267,783 B1 | 7/2001 | Letendre et al. |
| 6,270,524 B1 | 8/2001 | Kim |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,287,291 B1 | 9/2001 | Bigus et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,334,871 B1 | 1/2002 | Dor et al. |
| 6,340,366 B2 | 1/2002 | Wijay |
| 6,344,272 B1 | 2/2002 | Oldenburg et al. |
| 6,348,065 B1 | 2/2002 | Brown et al. |
| 6,350,252 B2 | 2/2002 | Ray et al. |
| 6,350,277 B1 | 2/2002 | Kocur |
| 6,357,104 B1 | 3/2002 | Myers |
| 6,361,558 B1 | 3/2002 | Hieshima et al. |
| 6,375,676 B1 | 4/2002 | Cox |
| 6,379,365 B1 | 4/2002 | Diaz |
| 6,383,171 B1 | 5/2002 | Gifford et al. |
| 6,394,995 B1 | 5/2002 | Solar et al. |
| 6,409,753 B1 | 6/2002 | Brown et al. |
| 6,415,696 B1 | 7/2002 | Erickeson et al. |
| 6,416,543 B1 | 7/2002 | Hilaire et al. |
| 6,419,693 B1 | 7/2002 | Fariabi |
| 6,425,898 B1 | 7/2002 | Wilson et al. |
| 6,428,811 B1 | 8/2002 | West et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,558,415 B2 | 5/2003 | Thompson |
| 6,562,067 B2 | 5/2003 | Mathis |
| 6,565,599 B1 | 5/2003 | Hong et al. |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,589,273 B1 | 7/2003 | McDermott |
| 6,592,549 B2 | 7/2003 | Gerdts et al. |
| 6,599,296 B1 | 7/2003 | Gillick et al. |
| 6,599,314 B2 | 7/2003 | Mathis |
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,613,074 B1 | 9/2003 | Mitelberg et al. |
| 6,629,992 B2 | 10/2003 | Bigus et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 | 12/2003 | Dusbabek et al. |
| 6,666,883 B2 | 12/2003 | Seguin et al. |
| 6,676,693 B1 | 1/2004 | Belding et al. |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |

(56) References Cited

U.S. PATENT DOCUMENTS

| | | |
|---|---|---|
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,743,219 B1 | 6/2004 | Dwyer et al. |
| 6,743,251 B1 | 6/2004 | Eder |
| 6,761,734 B2 | 7/2004 | Suhr |
| 6,776,771 B2 | 8/2004 | van Moorlegem et al. |
| 6,778,316 B2 | 8/2004 | Halas et al. |
| 6,790,227 B2 | 9/2004 | Burgermeister |
| 6,800,065 B2 | 10/2004 | Duane et al. |
| 6,825,203 B2 | 11/2004 | Pasternak et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |
| 6,893,417 B2 | 5/2005 | Gribbons et al. |
| 6,896,695 B2 | 5/2005 | Mueller et al. |
| 6,899,728 B1 | 5/2005 | Phillips et al. |
| 6,913,619 B2 | 7/2005 | Brown et al. |
| 6,918,928 B2 | 7/2005 | Wolinsky et al. |
| 6,939,376 B2 | 9/2005 | Shulz et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,004,964 B2 | 2/2006 | Thompson et al. |
| 7,005,454 B2 | 2/2006 | Brocchini et al. |
| 7,022,132 B2 | 4/2006 | Kocur |
| 7,029,493 B2 | 4/2006 | Majercak et al. |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,131,993 B2 | 11/2006 | Gregorich |
| 7,137,993 B2 | 11/2006 | Acosta et al. |
| 7,141,063 B2 | 11/2006 | White et al. |
| 7,147,655 B2 | 12/2006 | Chermoni |
| 7,147,656 B2 | 12/2006 | Andreas et al. |
| 7,169,172 B2 | 1/2007 | Levine et al. |
| 7,169,174 B2 | 1/2007 | Fischell et al. |
| 7,172,620 B2 | 2/2007 | Gilson |
| 7,175,654 B2 | 2/2007 | Bonsignore et al. |
| 7,182,779 B2 | 2/2007 | Acosta et al. |
| 7,192,440 B2 | 3/2007 | Andreas et al. |
| 7,208,001 B2 | 4/2007 | Coyle et al. |
| 7,208,002 B2 | 4/2007 | Shelso |
| 7,220,275 B2 | 5/2007 | Davidson et al. |
| 7,220,755 B2 | 5/2007 | Betts et al. |
| 7,223,283 B2 | 5/2007 | Chouinard |
| 7,238,197 B2 | 7/2007 | Sequin et al. |
| 7,241,308 B2 | 7/2007 | Andreas et al. |
| 7,244,336 B2 | 7/2007 | Fischer et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,351,255 B2 | 4/2008 | Andreas |
| 7,402,168 B2 | 7/2008 | Sanderson et al. |
| 7,534,449 B2 | 5/2009 | Saltzman et al. |
| 7,699,886 B2 | 4/2010 | Sugimoto |
| 7,824,439 B2 | 11/2010 | Toyokawa |
| 7,892,273 B2 | 2/2011 | George et al. |
| 7,918,881 B2 | 4/2011 | Andreas et al. |
| 7,938,851 B2 | 5/2011 | Olson et al. |
| 7,993,388 B2 | 8/2011 | Lee et al. |
| 8,070,794 B2 | 12/2011 | Issenmann |
| 8,157,851 B2 | 4/2012 | Andreas |
| 8,257,427 B2 | 9/2012 | Andersen et al. |
| 8,282,680 B2 | 10/2012 | Kao et al. |
| 8,317,850 B2 | 11/2012 | Kusleika |
| 2001/0001824 A1 | 5/2001 | Wu |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2001/0049549 A1 | 12/2001 | Boylan et al. |
| 2002/0007212 A1 | 1/2002 | Brown et al. |
| 2002/0032457 A1 | 3/2002 | Sirhan et al. |
| 2002/0035395 A1 | 3/2002 | Sugimoto |
| 2002/0037358 A1 | 3/2002 | Barry et al. |
| 2002/0045914 A1 | 4/2002 | Roberts et al. |
| 2002/0052642 A1 | 5/2002 | Cox et al. |
| 2002/0087186 A1 | 7/2002 | Shelso |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0123792 A1 | 9/2002 | Burgermeister |
| 2002/0128706 A1 | 9/2002 | Osypka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0165599 A1 | 11/2002 | Nasralla |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0013266 A1 | 1/2003 | Fukuda et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0105511 A1 | 6/2003 | Welsh et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0163155 A1 | 8/2003 | Haverkost et al. |
| 2003/0176909 A1 | 9/2003 | Kusleika |
| 2003/0191516 A1 | 10/2003 | Weldon et al. |
| 2003/0195609 A1 | 10/2003 | Berenstein et al. |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer |
| 2003/0225446 A1 | 12/2003 | Hartley |
| 2004/0015224 A1 | 1/2004 | Armstrong et al. |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0073290 A1 | 4/2004 | Chouinard |
| 2004/0087965 A1 | 5/2004 | Levine et al. |
| 2004/0088044 A1 | 5/2004 | Brown et al. |
| 2004/0093061 A1 | 5/2004 | Acosta et al. |
| 2004/0093067 A1 | 5/2004 | Israel |
| 2004/0093077 A1 | 5/2004 | White et al. |

(56) References Cited

U.S. PATENT DOCUMENTS

| | | |
|---|---|---|
| 2004/0098081 A1 | 5/2004 | Landreville et al. |
| 2004/0106979 A1 | 6/2004 | Goicoechea |
| 2004/0111145 A1 | 6/2004 | Serino et al. |
| 2004/0117008 A1 | 6/2004 | Wnendt et al. |
| 2004/0138737 A1 | 7/2004 | Davidson et al. |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas |
| 2004/0215331 A1 | 10/2004 | Chew et al. |
| 2004/0230285 A1 | 11/2004 | Gifford, III et al. |
| 2004/0243217 A1 | 12/2004 | Andersen et al. |
| 2004/0249434 A1 | 12/2004 | Andreas et al. |
| 2004/0249435 A1 | 12/2004 | Andreas et al. |
| 2004/0249439 A1 | 12/2004 | Richter et al. |
| 2005/0004657 A1 | 1/2005 | Burgermeister |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0055077 A1 | 3/2005 | Marco et al. |
| 2005/0075716 A1 | 4/2005 | Yan |
| 2005/0080474 A1 | 4/2005 | Andreas et al. |
| 2005/0080475 A1 | 4/2005 | Andreas et al. |
| 2005/0085897 A1 | 4/2005 | Bonsignore |
| 2005/0090846 A1 | 4/2005 | Pedersen et al. |
| 2005/0101624 A1 | 5/2005 | Betts et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0133164 A1 | 6/2005 | Fischer et al. |
| 2005/0137622 A1 | 6/2005 | Griffin |
| 2005/0143827 A1 | 6/2005 | Globerman et al. |
| 2005/0149159 A1 | 7/2005 | Andreas et al. |
| 2005/0149168 A1 | 7/2005 | Gregorich |
| 2005/0165378 A1 | 7/2005 | Heinrich et al. |
| 2005/0171568 A1 | 8/2005 | Duffy |
| 2005/0182477 A1 | 8/2005 | White |
| 2005/0209674 A1 | 9/2005 | Kutscher et al. |
| 2005/0209676 A1 | 9/2005 | Kusleika |
| 2005/0209680 A1 | 9/2005 | Gale et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0278011 A1 | 12/2005 | Peckham |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0177476 A1 | 8/2006 | Saffran |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0010869 A1 | 1/2007 | Sano |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0097574 A1 | 4/2008 | Andreas et al. |
| 2008/0125850 A1 | 5/2008 | Andreas et al. |
| 2008/0132989 A1 | 6/2008 | Snow et al. |
| 2008/0147162 A1 | 6/2008 | Andreas et al. |
| 2008/0177369 A1 | 7/2008 | Will et al. |
| 2008/0199510 A1 | 8/2008 | Ruane et al. |
| 2008/0208311 A1 | 8/2008 | Kao et al. |
| 2008/0208318 A1 | 8/2008 | Kao et al. |
| 2008/0234795 A1 | 9/2008 | Snow et al. |
| 2008/0234798 A1 | 9/2008 | Chew et al. |
| 2008/0234799 A1 | 9/2008 | Acosta et al. |
| 2008/0243225 A1 | 10/2008 | Satasiya et al. |
| 2008/0249607 A1 | 10/2008 | Webster et al. |
| 2008/0269865 A1 | 10/2008 | Snow et al. |
| 2009/0076584 A1 | 3/2009 | Mao et al. |
| 2009/0105686 A1 | 4/2009 | Snow et al. |
| 2009/0149863 A1 | 6/2009 | Andreas et al. |
| 2009/0228088 A1 | 9/2009 | Lowe et al. |
| 2009/0234428 A1 | 9/2009 | Snow et al. |
| 2009/0248137 A1 | 10/2009 | Andersen et al. |
| 2009/0248140 A1 | 10/2009 | Gerberding |
| 2009/0264979 A1 | 10/2009 | Kao et al. |
| 2009/0276030 A1 | 11/2009 | Kusleika |
| 2010/0004729 A1 | 1/2010 | Chew et al. |
| 2011/0022148 A1 | 1/2011 | Ruane et al. |
| 2011/0093056 A1 | 4/2011 | Kaplan et al. |
| 2011/0152996 A1 | 6/2011 | Snow et al. |
| 2013/0060321 A1 | 3/2013 | Kao et al. |
| 2013/0211494 A1 | 8/2013 | Snow et al. |
| 2014/0018899 A1 | 1/2014 | Snow et al. |

FOREIGN PATENT DOCUMENTS

| | | |
|---|---|---|
| DE | 1 963 0469 | 1/1998 |
| DE | 199 50 756 | 8/2000 |
| DE | 101 03 000 | 8/2002 |
| EP | 0 203 945 B2 | 12/1986 |
| EP | 0 274 129 B1 | 7/1988 |
| EP | 0 282 143 | 9/1988 |
| EP | 0 364 787 A1 | 4/1990 |
| EP | 0 505 686 | 9/1992 |
| EP | 0 533 960 | 3/1993 |
| EP | 0 596 145 | 5/1994 |
| EP | 0 696 447 A2 | 2/1996 |
| EP | 0 714 640 | 6/1996 |
| EP | 0 797 963 A2 | 10/1997 |
| EP | 0 947 180 | 10/1999 |
| EP | 1 254 644 A1 | 11/2002 |
| EP | 1 258 230 | 11/2002 |
| EP | 1 266 638 B1 | 12/2002 |
| EP | 1 277 449 | 1/2003 |
| EP | 1 290 987 A2 | 3/2003 |
| EP | 1 318 765 | 6/2003 |
| EP | 1 470 834 | 10/2004 |
| EP | 1 523 959 A2 | 4/2005 |
| EP | 1 523 960 A2 | 4/2005 |
| EP | 1 743 603 A2 | 1/2007 |
| GB | 2277875 A | 11/1994 |

(56) References Cited

FOREIGN PATENT DOCUMENTS

| | | |
|---|---|---|
| JP | 03-133446 | 6/1991 |
| JP | 07-132148 | 5/1995 |
| JP | 10-503663 | 4/1998 |
| JP | 10-295823 | 11/1998 |
| JP | 11-503056 T | 3/1999 |
| JP | 2935561 B2 | 8/1999 |
| JP | 2001-190687 | 7/2001 |
| JP | 2002-538932 T | 11/2002 |
| JP | 2004-121343 A | 4/2004 |
| WO | 94/27667 A1 | 12/1994 |
| WO | 95/26695 A2 | 10/1995 |
| WO | 95/29647 A2 | 11/1995 |
| WO | 96/26689 | 9/1996 |
| WO | 96/33677 | 10/1996 |
| WO | 96/37167 A1 | 11/1996 |
| WO | 96/39077 | 12/1996 |
| WO | 97/10778 | 3/1997 |
| WO | 97/46174 | 12/1997 |
| WO | 97/48351 | 12/1997 |
| WO | 98/20810 | 5/1998 |
| WO | 98/37833 | 9/1998 |
| WO | 98/58600 | 12/1998 |
| WO | 99/01087 | 1/1999 |
| WO | 99/65421 | 12/1999 |
| WO | 00/12832 A3 | 3/2000 |
| WO | 00/15151 A1 | 3/2000 |
| WO | 00/25841 | 5/2000 |
| WO | 00/32136 | 6/2000 |
| WO | 00/41649 | 7/2000 |
| WO | 00/50116 | 8/2000 |
| WO | 00/51525 A1 | 9/2000 |
| WO | 00/56237 | 9/2000 |
| WO | 00/62708 | 10/2000 |
| WO | 00/72780 | 12/2000 |
| WO | 01/26707 | 4/2001 |
| WO | 01/34063 | 5/2001 |
| WO | 01/70297 | 9/2001 |
| WO | 01/91918 | 12/2001 |
| WO | 02/060344 | 8/2002 |
| WO | 02/071975 | 9/2002 |
| WO | 02/085253 | 10/2002 |
| WO | 02/098326 | 12/2002 |
| WO | 03/022178 A1 | 3/2003 |
| WO | 03/047651 | 6/2003 |
| WO | 03/051425 | 6/2003 |
| WO | 03/075797 | 9/2003 |
| WO | 2004/017865 | 3/2004 |
| WO | 2004/043299 A1 | 5/2004 |
| WO | 2004/043301 | 5/2004 |
| WO | 2004/043510 | 5/2004 |
| WO | 2004/052237 A2 | 6/2004 |
| WO | 2004/087006 | 10/2004 |
| WO | 2004/091441 | 10/2004 |
| WO | 2005/009295 | 2/2005 |
| WO | 2005/013853 | 2/2005 |
| WO | 2005/023153 | 3/2005 |
| WO | 2006/036939 | 4/2006 |
| WO | 2006/047520 | 5/2006 |
| WO | 2007/035805 | 3/2007 |
| WO | 2007/053187 | 5/2007 |
| WO | 2007/146411 | 12/2007 |
| WO | 2008/005111 | 1/2008 |

OTHER PUBLICATIONS

Colombo, "The Invatec Bifurcation Stent Solution" Bifurcation Stents: Novel Solutions, TCT 2003, Washington: Sep. 15-19, 2003, 24 pages total.

Cooley et al., "Applications of Ink-Jet Printing Technology to BioMEMs and Microfluidic Systems," Proceedings, SPIE Conference on Microfluidics and BioMEMs, (Oct. 2001).

"Drug Delivery Stent With Holes Located on Neutral Axis" Research Disclosure, Kenneth Mason Publications, Hampshire, CB, No. 429, Jan. 2000, p. 13.

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," J Control Release. Sep. 19, 2003;92(1-2):83-91.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., "Parallel Production of Oligonucleotide Arrays Using Membranes and Reagent Jet Printing," BioTechniques 25:886-890 (Nov. 1998).

Tilley , "Biolimus A9-Eluting Stent Shows Promise," Medscape Medical News, Oct. 5, 2004; retrieved from the internet: <http://www.medscape.com/viewarticle/490621>, 2 pages total.

Weir et al., "Degradation of poly-L-lactide. Part 2: increased temperature accelerated degradation," Proc Inst Mech Eng H. 2004;218(5):321-30.

Supplementary European Search Report of EP Patent Application No. 05727731.1, dated Mar. 25, 2008, 2 pages total.

Supplementary European Search Report of EP Patent Application No. 05744136, dated Mar. 26, 2008, 3 pages total.

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

Supplementary European Search Report of EP Patent Application No. 07758831, dated Dec. 14, 2009.

International Search Report and Written Opinion of PCT Application No. PCT/US2008/061041, mailed Nov. 7, 2008, 13 pages total.

Intellectual Property Office of the Republic of China, First Office Action date of dispatch Oct. 26, 2011, 11 pages.

The State Intellectual Property Office of the People's Republic of China, Second Office Action date of dispatch Jul. 25, 2012, 23 pages.

Supplementary European Search Report of EP Patent Application No. 02804509, dated Dec. 13, 2006, 1 page total.

Supplementary European Search Report of EP Patent Application No. 04749567, dated Sep. 11, 2006, 3 pages total.

* cited by examiner

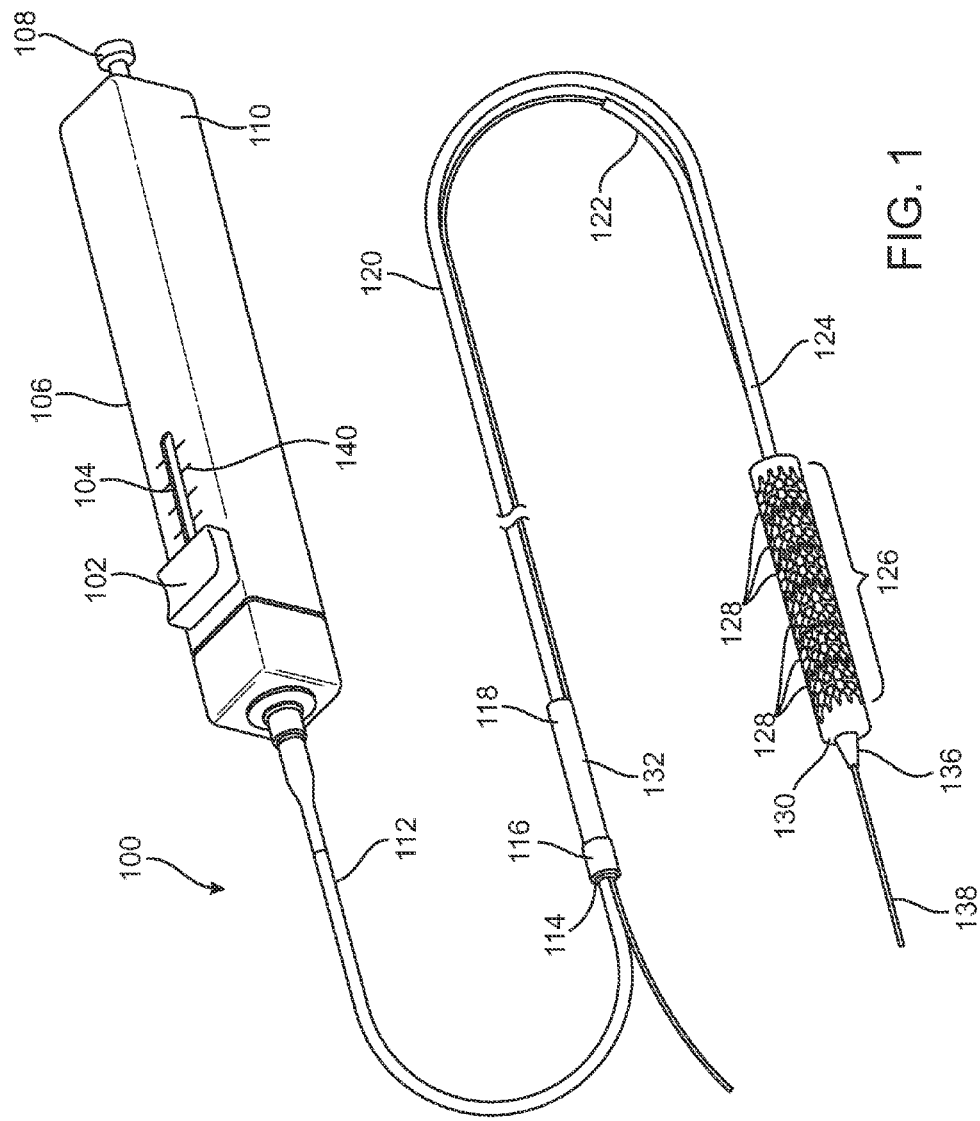

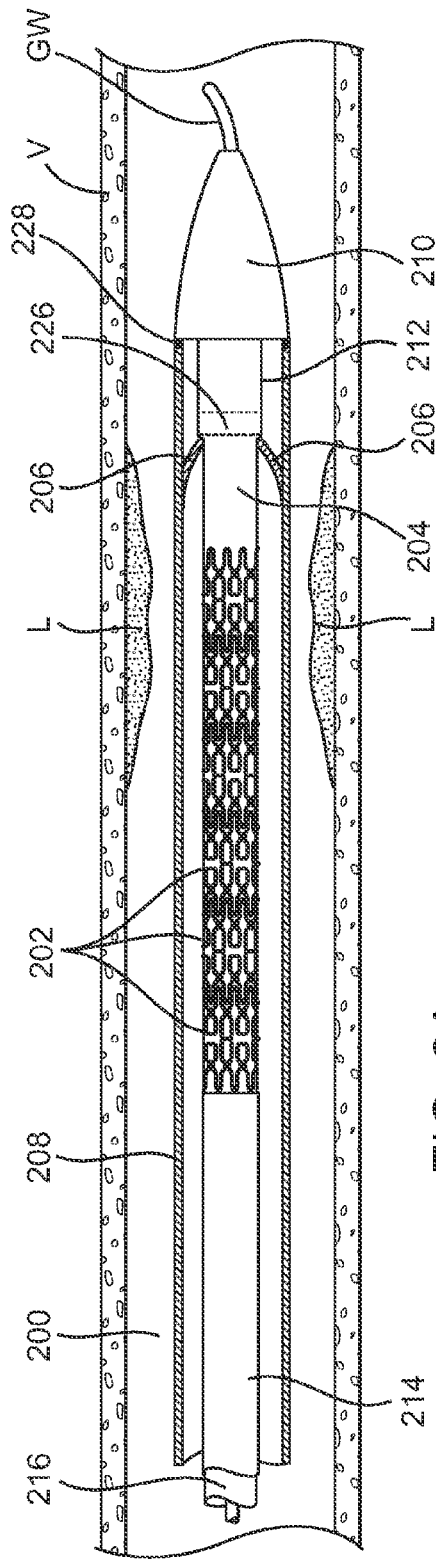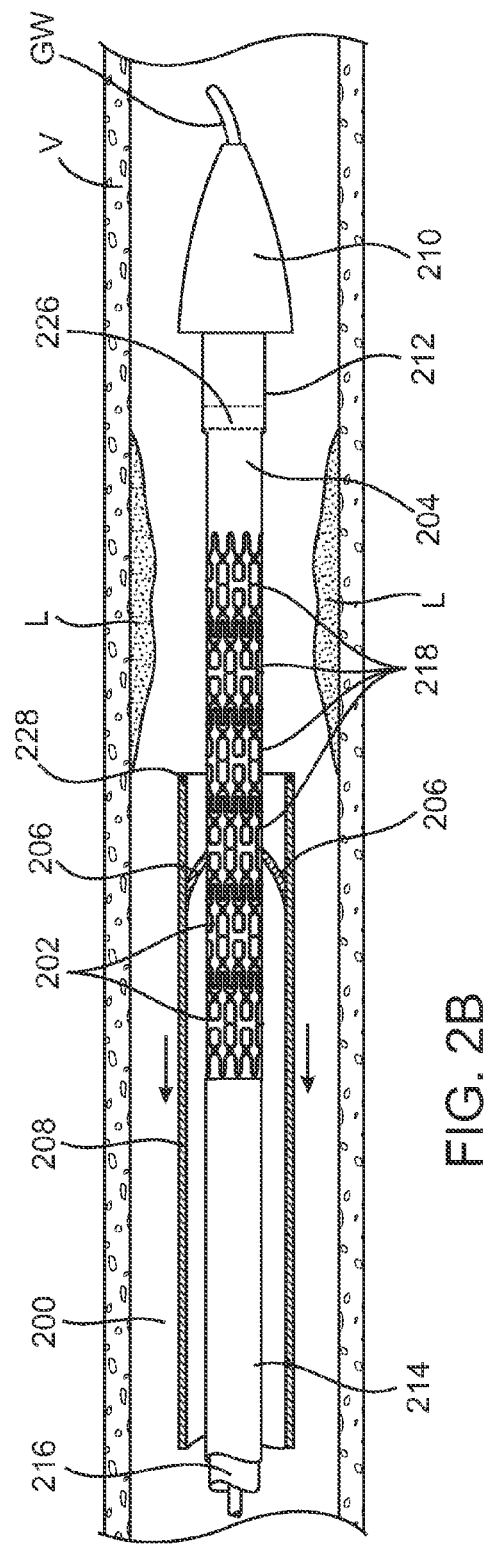
FIG. 2A
FIG. 2B

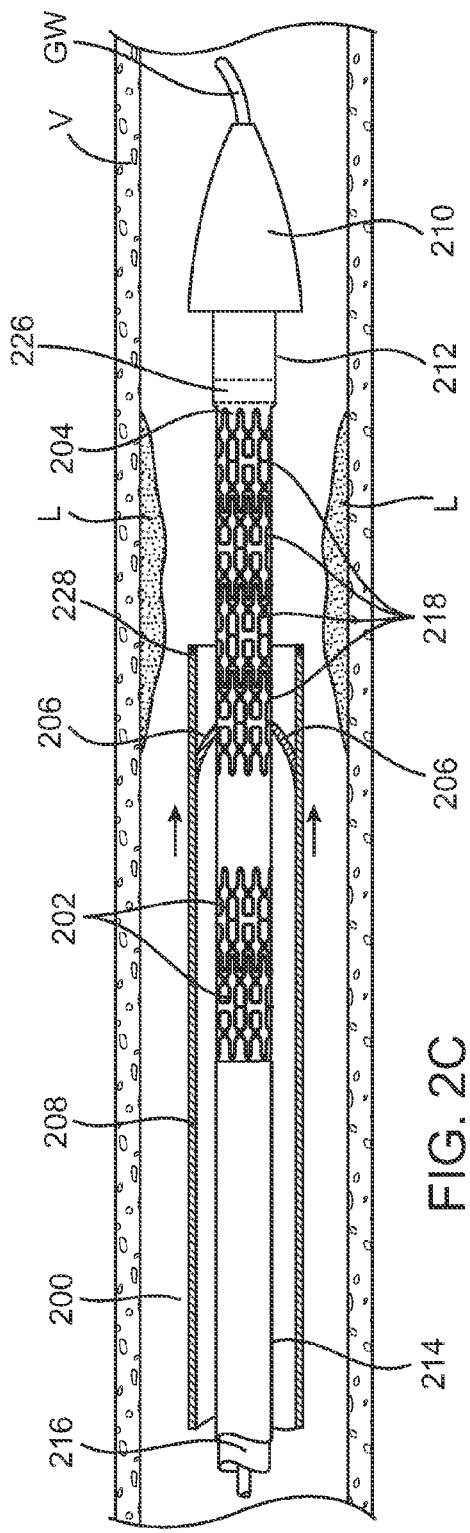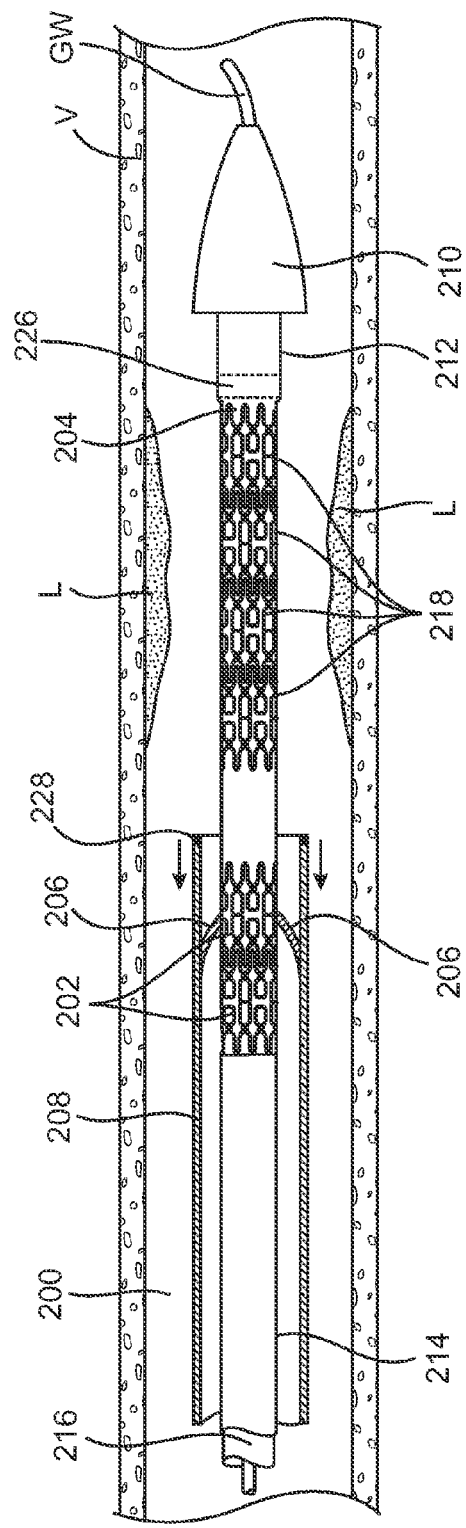

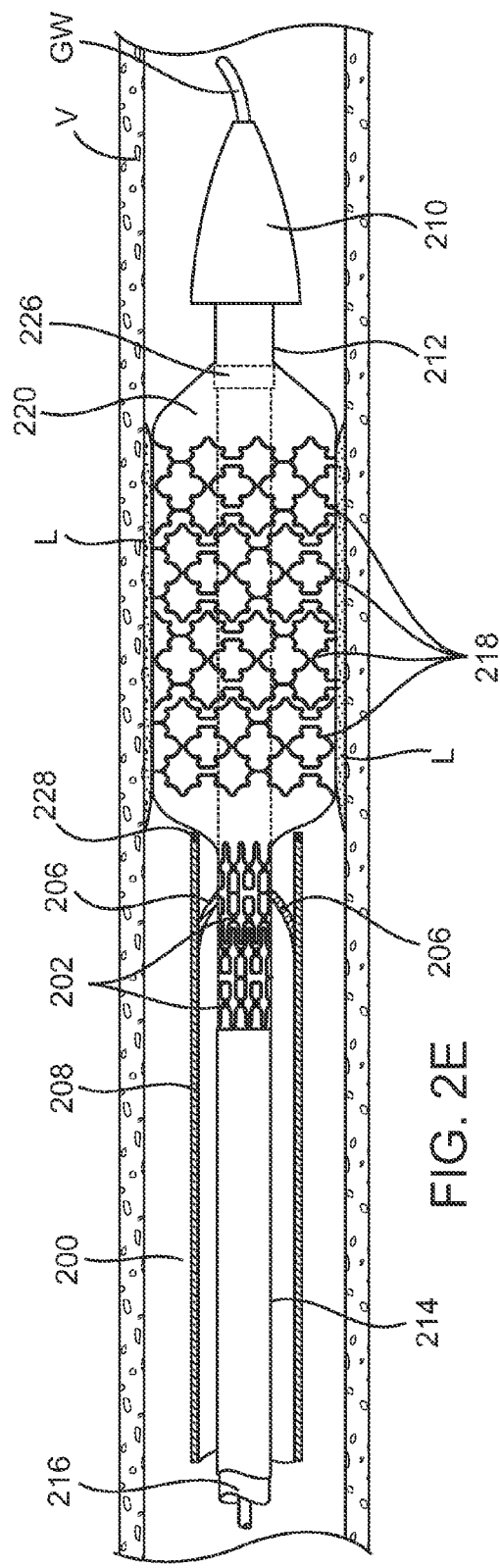
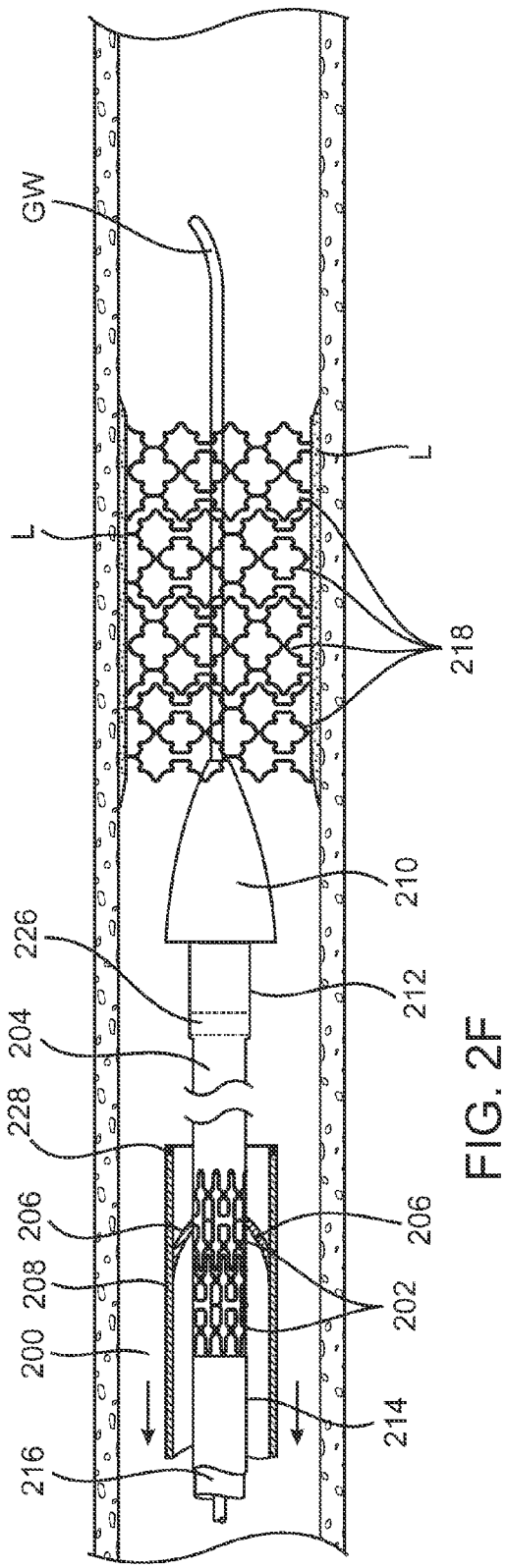

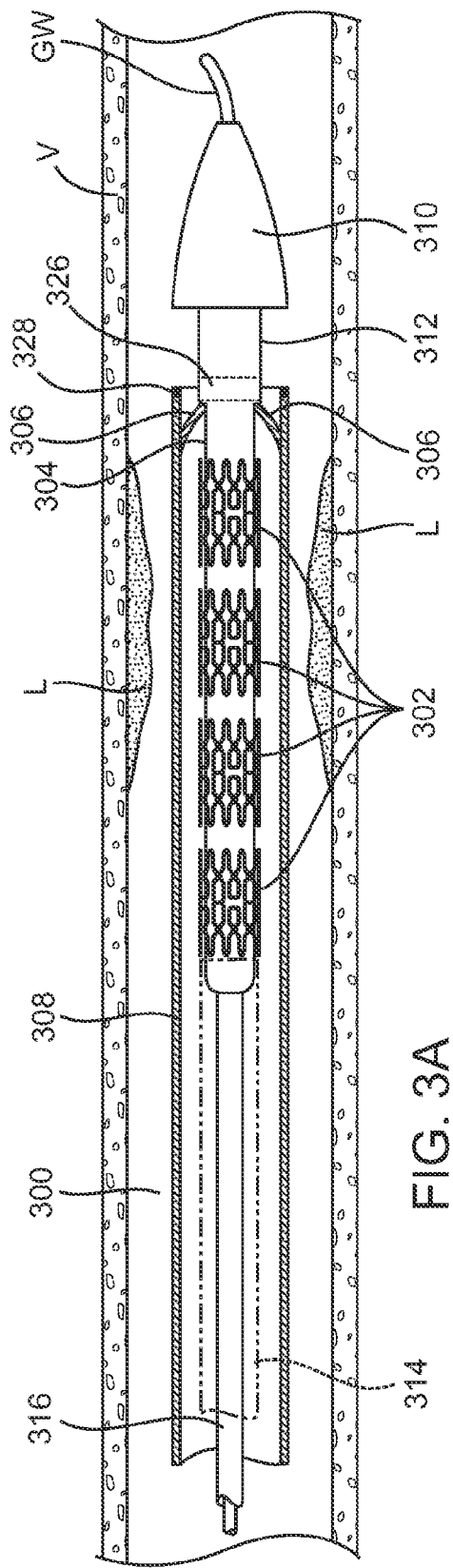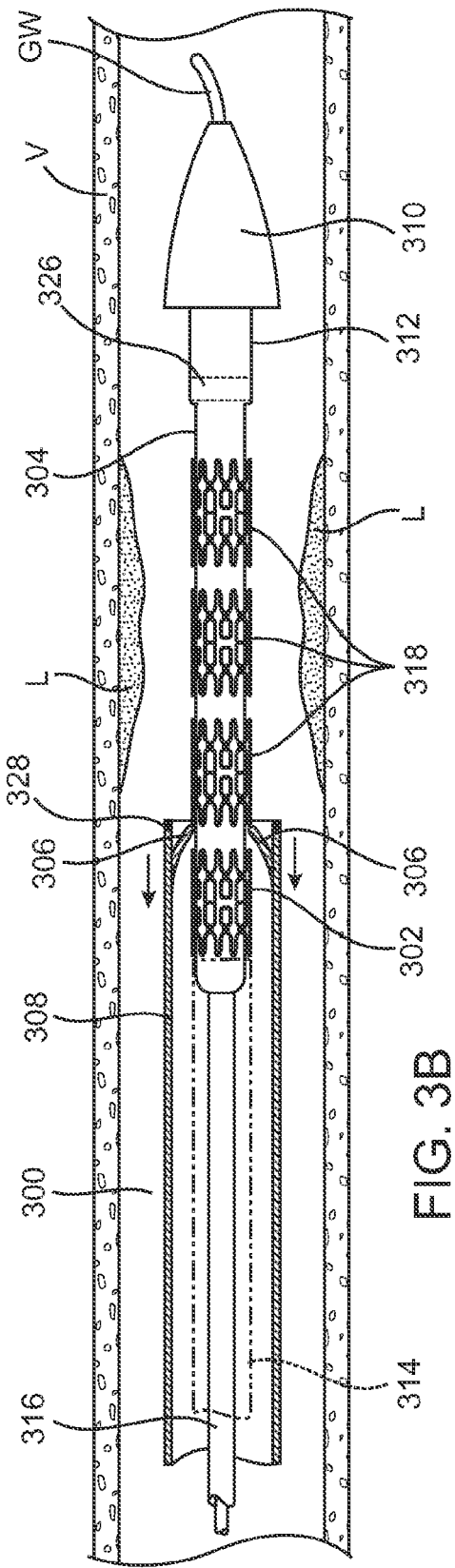

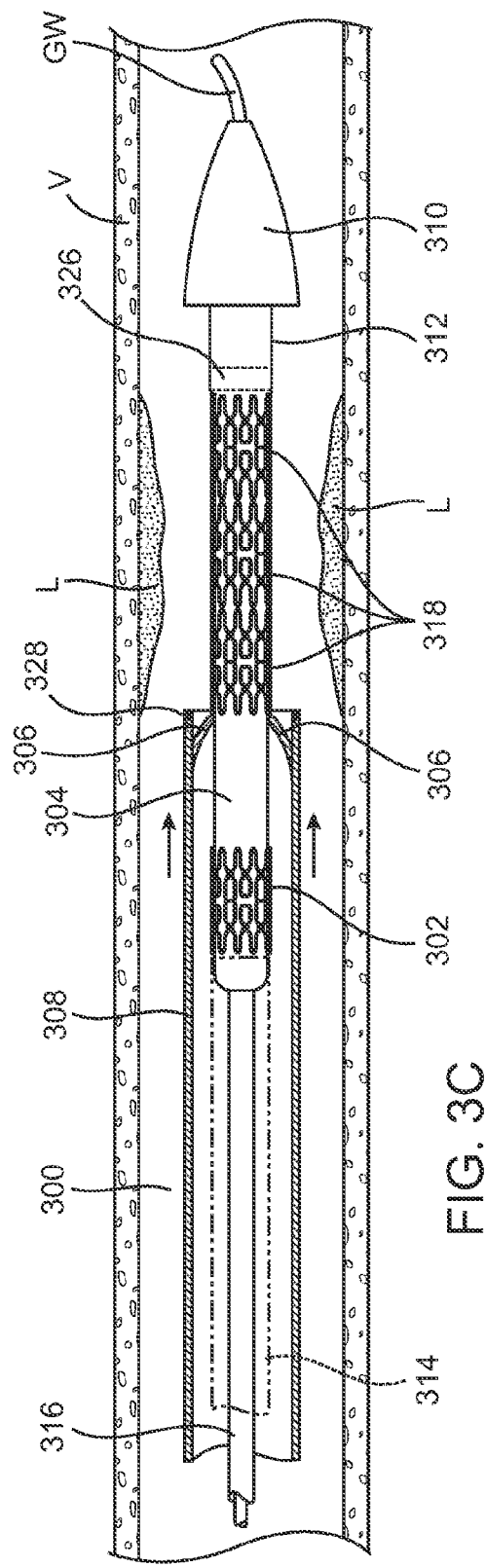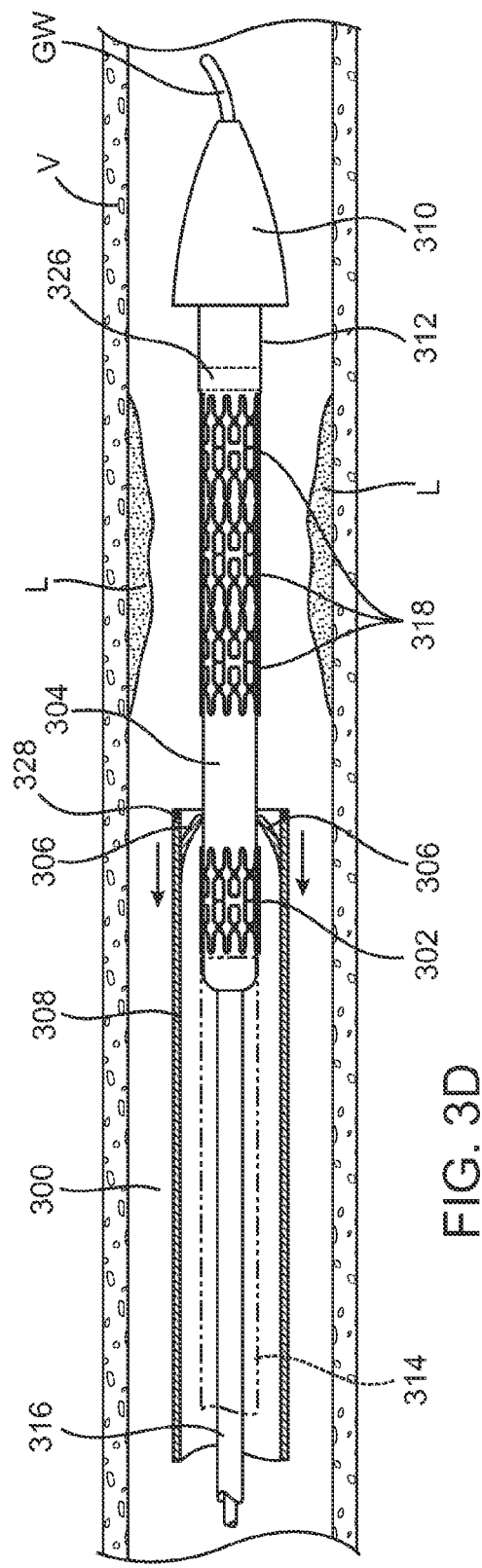
FIG. 3C                    FIG. 3D

CUSTOM LENGTH STENT APPARATUS

CROSS-REFERENCES TO RELATED APPLICATIONS

This application is a divisional of U.S. patent application Ser. No. 11/469,773, filed Sep. 1, 2006, which is a continuation-in-part of U.S. patent application Ser. No. 10/412,714, filed Apr. 10, 2003, which was a continuation-in-part of U.S. patent application Ser. No. 10/306,813, filed Nov. 27, 2002, which was a non-provisional of U.S. Patent Application Nos. 60/336,967 filed Dec. 3, 2001, and is also a non-provisional of U.S. Patent Application Ser. No. 60/364,389 filed on Mar. 13, 2002, the full disclosures of which are incorporated herein by reference.

BACKGROUND OF THE INVENTION

1. Field of the Invention

This invention relates generally to medical apparatus and methods, and more specifically to vascular catheters, stents and stent delivery systems for use in the coronary arteries and other vessels.

Stenting is an important treatment option for patients with vascular occlusive disease. The stenting procedure involves placing a tubular prosthesis at the site of a lesion, typically within a diseased coronary artery. The procedure is performed in order to maintain the patency of the artery and is often performed after a primary treatment such as angioplasty. Early stent results suffered from high rates of restenosis, i.e. the tendency for the stented coronary artery to become re-occluded following implantation of the stent. However, in recent years, restenosis rates have decreased substantially, due in part to drug eluting stents as well as other improvements in stent delivery methods and stent technology. As a result, the number of stent related procedures being performed worldwide continues to dramatically increase.

Stents are typically either self-expanding or balloon expandable and they are delivered to the coronary arteries using long, flexible vascular catheters typically inserted percutaneously through the patient's femoral artery. For self-expanding stents, the stent is simply released from the delivery catheter and it resiliently expands into engagement with the vessel wall. For balloon expandable stents, a balloon on the delivery catheter is expanded which expands and deforms the stent to the desired diameter, whereupon the balloon is deflated and removed, leaving the stent in place.

Current stent delivery technology suffers from a number of drawbacks which can make delivery of stents challenging. In particular, current stent delivery catheters often employ stents having fixed lengths. The proper selection of fixed length stents requires accurate knowledge of the lesion length being treated. While lesion length may be measured prior to stent deployment using angiography and fluoroscopy, these measurements are often inaccurate. Thus, if an incorrectly sized stent is introduced to a treatment site, then it must be removed from the patient along with the delivery catheter and replaced with a different device having the correct stent size. This prolongs the procedure, increases waste and results in a more costly procedure.

The use of "custom length" stents as an alternative to fixed length stents has been proposed. One such approach for providing a custom length stent has been to use segmented stents for treatment in which only some of the stents are deployed for treatment. Several exemplary systems are described in several copending, commonly assigned applications which are listed below. In these systems, the stent segments are deployed by selective advancement over the delivery catheter. After delivering an initial group of segments, the catheter may be repositioned to a new treatment site and a further group of segments can then be deployed. These systems enable treatment of multiple lesions with a single device and may contain up to fifty segments. While this technology represents a significant improvement over earlier stent delivery systems, in the case of smaller, more focal lesions or single lesions, only a small number of stent segments are needed and thus there is considerable waste when a large number of stent segments remain undeployed and end up being discarded at the end of the procedure.

Another challenge with existing "custom length" stent delivery systems is that to deliver multiple stent segments to multiple lesion sites requires an intricate delivery system that can be somewhat complex to use. Thus, a simpler delivery system that allows length customization with fewer prosthetic segments on the delivery catheter is desirable, especially for use in treating a single lesion.

For the above reasons as well as others, it would be desirable to provide improved prosthetic stents and delivery catheters. It would be particularly desirable to provide catheters which enable stent length to be customized yet have a minimal quantity of stent segments so as to treat common lesion lengths while minimizing stent segment waste. It is also desirable to provide a delivery system that is flexible and can track torturous vessels and that has a simple construction and is less costly and easy to use in deploying a selectable number of stent segments to a single treatment site.

2. Description of the Background Art

Prior publications describing catheters for delivering multiple segmented stents include: U.S. Publication Nos. 2004/0098081, 2005/0149159, 2004/0093061, 2005/0010276, 2005/0038505, 2004/0186551 and 2003/013266. Prior related unpublished co-pending U.S. patent applications include Ser. No. 11/148,713, filed Jun. 8, 2005, entitled "Devices and Methods for Operating and Controlling Interventional Apparatus"; Ser. No. 11/148,545, filed Jun. 8, 2005, entitled "Apparatus and Methods for Deployment of Multiple Custom-Length Prosthesis"; Ser. No. 11/344,464, filed Jan. 30, 2006, entitled "Apparatus and Methods for Deployment of Custom-Length Prostheses"; Ser. No. 60/784,309, filed Mar. 20, 2006, entitled "Apparatus and Methods for Deployment of Linked Prosthetic Segments"; and Ser. No. 11/462,951, filed Aug. 7, 2006, entitled "Custom Length Stent Apparatus." The full disclosures of each of these patents and applications are incorporated herein by reference.

BRIEF SUMMARY OF THE INVENTION

The invention generally provides for the delivery of prosthetic segments with a flexible delivery catheter capable of navigating torturous vessels such as the coronary arteries. The delivery catheter permits deployment of a selectable number of prosthetic segments at a single treatment site, thus allowing customization of prosthesis length while the delivery catheter is in a body lumen at a treatment site. Customization of prosthesis length in situ permits better matching of the prosthesis length to the lesion length being treated. The delivery catheter has a simplified design including a control mechanism on the catheter handle for selecting prosthetic segments for deployment and a stent valve or separator on the distal end of an outer sheath that facilitates deployment of the selected group of stent segments.

The terms "stent" and "stenting" are defined to include any of the array of expandable prostheses and scaffolds which are introduced into a lumen at a target treatment site and expanded in situ thereby exerting a radially outward force against the lumen wall. The prosthesis of the present invention comprises a closed or an open lattice structure and is typically fabricated from a malleable or elastic material. When a malleable material is used, such as stainless steel, gold, platinum, titanium, cobalt chromium and other alloys, the stent segments are typically expanded by balloon inflation, causing plastic deformation of the lattice so that it remains permanently deformed in the open position after deployment. When formed from an elastic material, including superelastic materials such as nickel-titanium alloys, the lattice structures are commonly constrained radially during delivery and upon deployment the constraining structure is removed, allowing the prosthesis to "self-expand" at the target site. The terms "stent," "prosthetic segment" and "stent segment" refer broadly to all radially expansible stents, grafts, and other scaffold-like structures which are intended for deployment within a body lumen.

In a first aspect of the invention, an apparatus for delivering prosthetic segments in a body lumen comprises an elongated flexible member having a proximal and distal end and a plurality of prosthetic segments releasably arranged axially along the elongated flexible member near the distal end. Additionally, an outer sheath is slidably disposed over at least a portion of the prosthetic segments and a separator is disposed on the outer sheath. The separator is adapted to engage the prosthetic segments, wherein the separator is adapted to be retracted proximally to slide over the prosthetic segments and advanced distally to engage at least one prosthetic segment and separate a proximal group of the prosthetic segments from a distal group of prosthetic segments which are to be deployed in the body lumen. Typically, the separator exerts substantially greater axial force against the prosthetic segments when the separator is advanced distally than when the separator is retracted proximally.

In some embodiments, the apparatus further comprises a backstop element disposed on the elongated flexible member that is adapted to prevent proximal movement of the prosthetic segments when the separator is retracted proximally over the prosthetic segments. The backstop element may be a tube slidably disposed on the elongated flexible member or it may be an annular flange or a balloon. In some embodiments, the backstop element may comprise a compliant spacer. Other embodiments further comprise a stopping member disposed on the distal end of the elongated flexible member and adapted to stop distal movement of the prosthetic segments when the separator is advanced distally with the prosthetic segments.

In some embodiments, the prosthetic segments are balloon expandable, while in others, the prosthetic segments are self-expanding. The plurality of prosthetic segments usually have a length in the range from about 2 mm to 10 mm, and often the length is about 3 mm to 6 mm long. The prosthetic segments may have interleaved ends prior to deployment or they may be spaced apart prior to deployment to allow the separator to engage the segments at their proximal ends. Typically, the prosthetic segments are initially spaced proximally from the distal end of the elongate flexible member to allow the distal group of prosthetic segments to be advanced distally by the separator. Prosthetic segments often carry a therapeutic agent that is adapted to being released therefrom. Typically, this agent is an anti-restenosis agent. An expandable member is often a part of the apparatus located near the distal end of the elongated flexible member. In many instances, the expandable member is a balloon.

The separator is adapted to exert substantially greater axial force against the prosthetic segments when the separator is advanced distally than when the separator is retracted proximally. The term "separator" as used herein also may be referred to as a "stent valve" or "valve member." In some embodiments, the separator comprises a plurality of resilient fingers projecting radially inward. Usually, at least some of these fingers are inclined so that their free ends point distally, allowing the fingers to pass over the prosthetic segments as the separator is retracted proximally but to engage a prosthetic segment when the separator is advanced distally. In some cases, the fingers are composed of metal and in other cases they may be composed of a polymer or other suitable resilient material.

The fingers may be shaped in a variety of ways in order to engage with or slide over a stent segment. In some embodiments, at least some of the fingers comprise a radiused end substantially matching the curvature of the surface of the prosthetic segment. The radiused end provides a greater contact surface which facilitates engagement between the prosthetic segments and the separator as the separator is advanced distally while still allowing the separator to pass over the prosthetic segments during proximal retraction of the separator. Some embodiments of the separator may further comprise a hinge coupled to the resilient finger to allow the resilient fingers to deflect radially to facilitate passage of the separator over the prosthetic segments when the separator is retracted proximally.

In other embodiments, the separator comprises an annular flange which may be tapered. In yet other embodiments, the separator may comprise a tapered conical nose, a compliant sharp edge, or a plurality of inclined ramps disposed on an inner surface of the outer sheath. These ramps may be separated by about 90°. Other separators may be sufficiently flexible to be deflected outwardly during inflation of a balloon on the delivery apparatus and that is also adapted to automatically provide a spacing between prosthetic segments selected for delivery and those remaining with the delivery apparatus. This spacing is necessary to allow a balloon taper to form during balloon inflation. In other embodiments, the separator is a wire-like coil. In all stent valve embodiments, the valves are adapted to slide over the prosthetic segments without damaging or removing any coatings, such as a drug coating, that may be placed on the surfaces of the stent segments.

In another aspect of the present invention, a method for delivering prosthetic segments to a body lumen comprises introducing a plurality of prosthetic segments releasably arranged axially along an elongated flexible member, into a body lumen having a lesion with a lesion length at a first treatment site. A separator is retracted proximally relative to a group of prosthetic segments selected for delivery, with the selected prosthetic segments having a combined length that matches the lesion length. The separator is then advanced distally so that the separator engages a prosthetic segment in the selected group and separates the group of prosthetic segments from one or more remaining segments. The selected group of prosthetic segments is then exposed so that they are radially unconstrained from expansion and then they are deployed at the first treatment site. Some embodiments may also comprise adding prosthetic segments to the selected group by advancing the separator distally a second time.

In yet another aspect of the present invention, a method for selectively delivering prosthetic segments to a treatment region in a body lumen comprises advancing a delivery catheter through the body lumen to the treatment region, wherein a plurality of prosthetic segments are disposed axially along the deliver catheter. A separator is then retracted over a first group of one or more prosthetic segments. The separator is then advanced distally so as to separate the first group of prosthetic segments from any remaining prosthetic segments. A balloon disposed on the delivery catheter is then inflated so as to deploy the first group of prosthetic segments while any remaining segments stay with the delivery catheter. In some embodiments, the method may further comprise adding prosthetic segments to the first group by advancing the separator distally a second time.

The prosthetic segments may be either balloon expandable or self-expanding. When the prosthetic segments are balloon expandable, deploying the selected group of segments comprises plastically deforming them, in most cases with a balloon.

In many instances, the prosthetic segments carry a therapeutic agent adapted to being released therefrom and the segments are spaced proximally from a distal end of the elongated flexible member. Often, the agent comprises an anti-restenosis agent. Additionally, the plurality of prosthetic segments commonly have a length in the range from about 2 mm to about 10 mm and preferably the length is about 3 mm to 6 mm long. In some cases, the prosthetic segments have interleaved ends prior to deployment while in other cases, the segments are spaced apart prior to deployment to allow the separator to engage the segments at their proximal ends. In still other embodiments, the method may comprise moving the prosthetic segments closer together when the separator is advanced distally, while in other embodiments the prosthetic segments are spaced proximally from the distal end of the elongated flexible member and the group of prosthetic segments selected for delivery is advanced toward the distal end of the elongate flexible member by a separator.

In preferred aspects of the method, the separator exerts substantially greater axial force against the prosthetic segments when the separator is advanced distally than when the separator is retracted proximally. Some embodiments comprise a separator having a plurality of resilient fingers projecting radially inward. Often, these fingers are inclined so that free ends of the fingers point distally allowing the fingers to pass over the prosthetic segments as the separator is retracted proximally but to engage a prosthetic segment when the separator is advanced distally. In some instances, at least some of the fingers are composed of metal, while in other embodiments, some of the fingers may be composed of a polymer.

In some embodiments of the method, at least some of the fingers comprise a radiused end substantially matching the curvature of the surface of the prosthetic segment thereby providing greater contact surface so as to facilitate engagement between the prosthetic segments and the separator as the separator is advanced distally while allowing the separator to pass over the prosthetic segments during proximal retraction of the separator. The separator may further comprise a hinge coupled to the resilient fingers which deflect radially outward over the prosthetic segments when the separator is retracted proximally.

In other embodiments, the separator comprises an annular flange or conical nose, either of which may be tapered. In other embodiments, the separator comprises a plurality of inclined ramps disposed on an inner surface of an outer sheath. Typically, the inclined ramps are separated by about 90°. In some embodiments, the separator comprises a compliant sharp edge or the separator may deflect outwardly during balloon inflation. Some separators may be a wire-like coil.

In some aspects of the method, advancing the separator distally comprises advancing an outer sheath distally, while in other aspects, advancing the separator distally comprises retracting the elongated flexible member proximally. Additionally, in some aspects of the method, exposing the selected group of prosthetic segments comprises proximally retracting an outer sheath slidably disposed along the elongated flexible member. In other aspects, a backstop element is disposed on the elongated flexible member and it prevents proximal movement of the prosthetic segments when the separator is retracted. Sometimes the backstop element is a tube slidably disposed on the elongated flexible member, or the backstop may be an annular flange or a balloon. In some embodiments, the backstop element may comprise a compliant spacer. In still other embodiments, a stopping member is disposed on the distal end of the elongated flexible member and this member prevents distal movement of the prosthetic segments when the separator is advanced distally. In all aspects of the method the separator or stent valve is adapted to slide over the prosthetic segments without damaging or removing any coatings, such as a drug coating, that may be placed on the surfaces of the stent segments.

These and other embodiments are described in further detail in the following description related to the appended drawing figures.

BRIEF DESCRIPTION OF THE DRAWINGS

FIG. 1 is a perspective view of a stent delivery catheter in accordance with one embodiment of the present invention.

FIGS. 2A-2G show selection and deployment of prosthetic stent segments in accordance with an exemplary embodiment.

FIGS. 2H-2J illustrate alternative embodiments of stent backstops.

FIGS. 3A-3E show selection and deployment of prosthetic stent segments in accordance with another exemplary embodiment.

DETAILED DESCRIPTION OF THE INVENTION

Figure 2G:
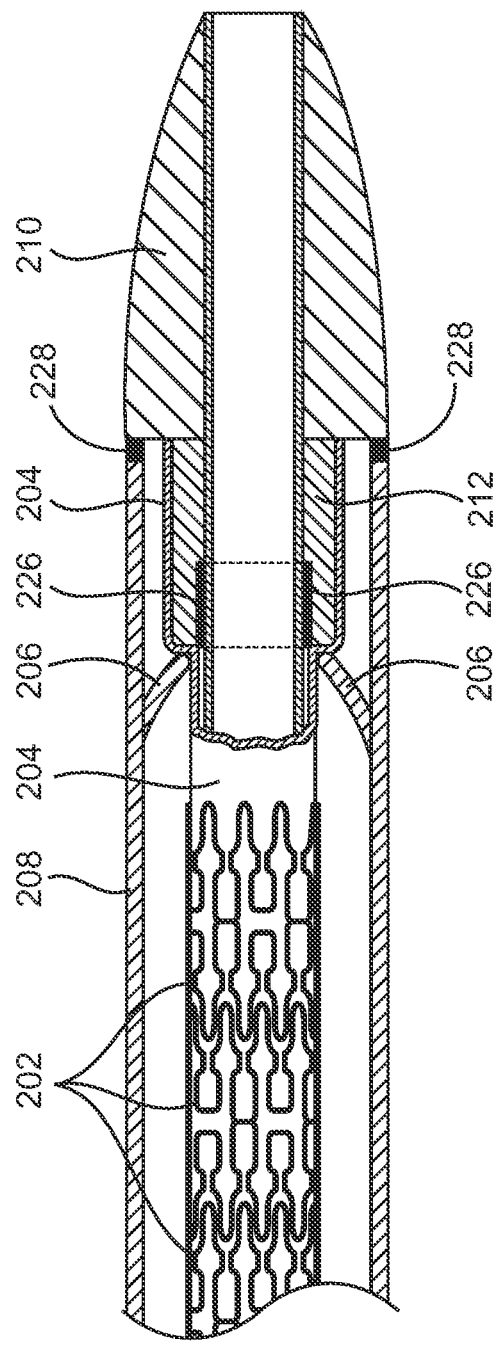

Referring now to FIG. 1, a stent delivery catheter 100 comprises a catheter shaft 120 with an outer sheath 124 slidably disposed over an inner shaft 216 (seen in FIG. 2A). An inflatable balloon 130, is mounted on the inner shaft 216 and is exposed by retracting sheath 124 relative to the inner shaft 216. A tapered nosecone 136, composed of a soft elastomeric material to minimize trauma to the vessel during advancement of the delivery catheter 100, is attached distally of the inflatable balloon 130 to the inner shaft 216. Prosthesis 126 comprises a plurality of prosthetic segments 128 mounted over the inflatable balloon 130 for expansion. A guidewire tube 122 is slidably positioned through sheath 124 proximal to the inflatable balloon 130. A guidewire 138 is positioned slidably through guidewire tube 122, inflatable balloon 130 and nosecone 136, and extends distally thereof. FIG. 1 illustrates the stent delivery catheter 100 and FIG. 2A shows various elements of the delivery catheter 100 in greater detail.

In FIG. 2A, a stent delivery catheter 200 is slidably disposed over the guidewire GW into the vessel V so that the nosecone 210 is distal to the lesion L. Stent segments 202 having interleaved ends in engagement with each other are disposed over expandable member 204 and covered by outer sheath 208. In this embodiment, six stent segments 202 are disposed on the stent delivery catheter 200. The segments 202 are positioned over balloon 204 leaving a distal portion of the balloon 204 free of any prosthetic segments 202. This uncovered region of the balloon is necessary since the prosthetic segments selected for delivery are advanced distally over this region during their deployment. A stopping member 212 disposed near the distal end of balloon 204 prevents the stent segments 202 from being advanced too far distally which could result in the prosthetic segments 202 falling off of the delivery catheter 200. The stopping member 212 is typically an annular flange that extends radially outward to prevent displacement of the prosthetic segments 202 beyond the stopping member 212. Often, balloon 204 is attached to the outer surface of stopping member 212. This prevents stent segments 202 from being advanced distally over the tapered portion of balloon 204 which forms during inflation, and thus ensures uniform expansion of stent segments 202 during deployment. FIG. 2G highlights the delivery catheter 200 around the stent stop 212 region. Additional details on stent stop 212 are described in co-pending U.S. patent application Ser. No. 10/884,616, filed Jul. 2, 2004, entitled "Apparatus and Methods for Positioning Prostheses for Deployment from a Catheter," the full disclosure of which is incorporated herein by reference.

A handle 106 on the proximal portion of the delivery catheter 100 is attached to a proximal end 112 of sheath 124 as seen in FIG. 1. The handle performs several functions, including retracting and advancing the sheath 124 thereby exposing prosthetic segments 128 and allowing the prosthetic segments 128 to be delivered. Additionally, using the handle 106 to displace the outer sheath 124 permits creation of a spacing between prosthetic segments 128 selected for delivery and the segments 128 that will remain with the delivery catheter 100. This gap or spacing between segments 128 permits proper balloon 130 inflation and will be described below in further detail along with the handle structure and operation.

Handle 106 includes a housing 110 which encloses the internal components of the handle 106. Handle 106 allows a physician operator to select a fixed retraction distance for outer sheath 124 which determines the length of the prosthesis 126 (number of prosthetic segments) to be deployed. The handle also permits connection of balloon 130 to an inflation source. The inner shaft 216 (FIG. 2A) is preferably fixed to the handle housing 110, while the outer sheath 124 is coupled to slide mechanism 102 so as to be retracted and advanced relative to handle 106. An adaptor 108 is attached to handle 106 at its proximal end and is fluidly coupled to the inner shaft 216 in the interior of the housing of handle 106. The adaptor 108, preferably a Luer connector, is configured to be fluidly coupled with an inflation device which may be any commercially available balloon inflation device such as those sold under the trade name "Indeflator™," manufactured by Abbott (formerly Guidant Corporation of Santa Clara, Calif.). The adaptor is in fluid communication with the inflatable balloon 130 via an inflation lumen in the inner shaft 216 to permit inflation of the inflatable balloon 130.

Additionally, a control mechanism on the handle 106 includes a slide mechanism 102 that translates along calibrated slot 104. Slide mechanism 102 is coupled with outer sheath 124 and is adapted to retract or advance the sheath 124 a selected distance. The selected distance is established by sliding slide mechanism 102 along slot 104 to permit exposure of a selected number of prosthetic segments 128 on the distal end of delivery catheter 100. The slide mechanism 102 includes visual markers 140 so that an operator can easily determine how many stent segments have been selected. Additionally, slide mechanism 102 may provide audible or tactile feedback to the operator to facilitate operation of the stent delivery catheter 100 without requiring direct visualization during operation. Additional details on materials and construction of handle 106 and housing 110 are described in co-pending U.S. patent application Ser. No. 11/148,713, filed Jun. 8, 2005, entitled "Devices and Methods for Operating and Controlling Interventional Apparatus," co-pending United States Publication No. 2005/0149159, entitled "Devices and Methods for Controlling and Indicating the Length of an Interventional Element," and application Ser. No. 11/462,951, filed Aug. 7, 2006, entitled "Custom Length Stent Apparatus," the full disclosures of which are incorporated herein by reference.

Outer sheath 124 and guidewire 138 each extend through a slider assembly 132 slidably disposed on the catheter body 120 at a point between handle 106 and expandable member 130. The slider assembly 132 is adapted for insertion into and sealing with a hemostasis valve, such as on an introducer sheath or guiding catheter, while still allowing relative movement of the outer sheath 124 relative to the slider assembly 132. The slider assembly 132 includes a slider tube 118, a slider body 116, and a slider cap 114.

Outer sheath 124 may be composed of any of a variety of biocompatible materials, such as but not limited to a polymer like PTFE, FEP, polyimide, Pebax, or Nylon and may be reinforced with a metallic or polymeric braid to resist radial expansion of inflatable balloon 130, and/or the like. Inflatable balloon 130 may be formed of a semi-compliant polymer such as Pebax, Nylon, polyurethane, polypropylene, PTFE or other suitable polymers. Additional aspects of the luminal prosthesis delivery system are described in U.S. patent application Ser. No. 10/306,813, filed Nov. 27, 2002; U.S. patent application Ser. No. 10/637,713, filed Aug. 8, 2003; U.S. patent application Ser. No. 10/738,666, filed Dec. 16, 2003; U.S. patent application Ser. No. 11/104,305, filed Apr. 11, 2005; and U.S. application Ser. No. 11/148,585, filed Jun. 8, 2005, the full disclosures of which are hereby incorporated by reference.

Delivery catheter 100 also includes a separator or "stent valve" disposed near the distal end of the sheath 124 and an exemplary embodiment of this is seen in FIG. 2A. In FIG. 2A, outer sheath 208 is advanced fully distally, covering the plurality of prosthetic segments 202 which are disposed over expandable member 204. Expandable member 204 acts as a carrier which supports the prosthetic segments 202. Separator 206 is located a distance from the distal end of outer sheath 208 typically one-half to twice the length of a prosthetic segment 202 and more preferably from about one to 1.5 times the prosthetic segment 202 length. This corresponds to a distance of about 3 mm to 10 mm.

Separator 206 contacts and engages prosthetic segments 202. As shown in FIG. 2A, separator 206 includes distally inclined resilient fingers configured to frictionally engage stent segments 202 when outer sheath 208 is advanced distally, while separator 206 is also able to slide over prosthetic segments 208 when the separator 206 is retracted distally. The separator 206 may be a polymeric or metallic material integrally formed with outer sheath 208 or may be bonded or otherwise mounted to the interior of the outer sheath 208. The geometry of separator 206 can also be toroidal with a circular or ovoid cross-section (like an O-ring) or the separator 206 may have another cross-sectional shape such as triangular, trapezoidal, pyramidal, or other shapes as described in embodiments discussed more fully herein below. The separator 206 can be a polymer such as silicone or urethane, sufficiently soft, compliant and resilient to provide frictional engagement with stent segments 202, in some embodiments without damaging any coating deposited thereon, including drug coatings. The separator 206 extends radially inwardly a sufficient distance to engage the exterior of stent segments 202 with sufficient force to allow the stent segments selected for delivery to be advanced distally with outer sheath 208 so as to create a spacing relative to those stent segments remaining with the outer sheath 208. Other exemplary embodiments of separators are discussed herein below and in particular with respect to FIGS. 5A-13. Additional aspects of separator 206 are described in U.S. patent application Ser. No. 10/412, 714, filed Apr. 10, 2003 and U.S. patent application Ser. No. 11/344,464, filed Jan. 30, 2006, the contents of which were previously incorporated herein by reference.

Prosthesis 126 in FIG. 1 is composed of one or more prosthetic segments 128. Prosthetic stent segments 128 are disposed over an inflation balloon 130. Each stent segment is about 2-20 mm in length, more typically about 2-10 mm in length and preferably being about 2-8 mm in length. Usually 2-20, more typically 2-10 and preferably 2-6 stent segments 30 may be positioned axially over the inflation balloon 130 and the inflation balloon 130 has a length suitable to accommodate the number of stent segments. Stent segments 128 may be positioned in direct contact with an adjacent stent segment or a space may exist between segments. Furthermore, the stent segments 128 may be deployed individually or in groups of two or more at a single treatment site within the vessel lumen.

Prosthetic stent segments 128 are preferably composed of a malleable metal so they may be plastically deformed by inflation balloon 130 as they are radially expanded to a desired diameter in the vessel at the target treatment site. The stent segments 128 may also be composed of an elastic or superelastic shape memory alloy such as Nitinol so that the stent segments 128 self-expand upon release into a vessel by refraction of the outer sheath 124. In this case, an inflation balloon 130 is not required but may still be used for predilation of a lesion or augmenting expansion of the self-expanding stent segments (e.g. postdilation or tacking). Other materials such as biocompatible polymers may be used to fabricate prosthetic stent segments and these materials may further include bioabsorbable or bioerodable properties.

Stent segments 128 may have any of a variety of common constructions, such as but not limited to those described in U.S. patent application Ser. No. 10/738,666 filed Dec. 16, 2003, which was previously incorporated by reference. Constructions may include for example, closed cell constructions including expansible ovals, ellipses, box structures, expandable diamond structures, etc. In addition, the closed cells may have complex slotted geometries such as H-shaped slots, I-shaped slots, J-shaped slots, etc. Suitable open cell structures include zigzag structures, serpentine structures, and the like. Such conventional stent structures are well described in the patent and medical literature. Specific examples of suitable stent structures are described in the following U.S. patents, the full disclosures of which are incorporated herein by reference: U.S. Pat. Nos. 6,315,794; 5,980,552; 5,836,964; 5,527,354; 5,421,955; 4,886,062; and 4,776,337.

In preferred embodiments, prosthetic stent segments 128 may be coated, impregnated, infused or otherwise coupled with one or more drugs that inhibit restenosis, such as Rapamycin, Everolimus, Paclitaxel, analogs, prodrugs, or derivatives of the aforementioned, or other suitable agents, preferably carried in a durable or bioerodable polymeric carrier. Alternatively, stent segments 128 may be coated with other types of drugs or therapeutic materials such as antibiotics, thrombolytics, anti-thrombotics, anti-inflammatories, cytotoxic agents, anti-proliferative agents, vasodilators, gene therapy agents, radioactive agents, immunosuppressants, chemotherapeutics and/or stem cells. Such materials may be coated over all or a portion of the surface of stent segments 128, or stent segments 128 may have a porous structure or include apertures, holes, channels, or other features in which such materials may be deposited.

Referring now to FIGS. 2A-2G, the deployment of selected prosthetic segments to treat a lesion is shown in accordance with an exemplary embodiment. While the embodiment will be described in the context of a coronary artery stent procedure, it should be understood that the invention may be employed in any variety of blood vessels and other body lumens in which stents or tubular prostheses are deployed, including the carotid, femoral, iliac and other arteries and veins, as well as non-vascular body lumens, such as the ureter, urethra, fallopian tubes, the hepatic duct and the like. A guide catheter (not illustrated) is first inserted into a peripheral artery such as the femoral artery, typically using a percutaneous procedure such as the Seldinger technique or by surgical cutdown, and then advanced to the ostium of the right or left coronary artery. Guidewire GW is then inserted through the guiding catheter and advanced into the target vessel V where a lesion L to be treated is located. The proximal end of guidewire GW is then inserted through nosecone 210 and guidewire tube 122 (seen in FIG. 1) which is outside the patient's body.

FIG. 2A shows stent delivery catheter 200 slidably advanced over the guidewire GW into the vessel V so that the nosecone 210 is distal to the lesion L. Stent segments 202 having interleaved ends in engagement with each other are disposed over expandable member 204, here a balloon, and covered by outer sheath 208. In this embodiment, six stent segments 202 are disposed on the stent delivery catheter 200. The segments 202 are positioned over balloon 204 leaving a distal portion of the balloon 204 free of any prosthetic segments 202. This uncovered region is necessary because the group of prosthetic segments selected for delivery will be advanced distally over this region during deployment. A stopping member 212 disposed near the distal end of inner shaft 216 prevents the stent segments from being advanced too far distally which could result in the prosthetic segments 202 falling off of the delivery catheter 200. The stopping member 212 is typically an annular flange that extends radially outward to prevent displacement of the prosthetic segments 202 beyond the stopping member 212. Often, balloon 204 is attached to the outer surface of stopping member 212. This prevents stent segments 202 from being advanced distally over the tapered portion of balloon 204 which forms during inflation, and thus ensures uniform expansion of stent segments 202 during deployment. FIG. 2G highlights the area around stent stopping member 212 in greater detail.

Additionally, outer sheath 208 has a high circumferential strength, or hoop strength, near separator 206 such that the distal portion of the outer sheath 208 is able to prevent the expandable member 204 from expanding when the outer sheath 208 and separator 206 are extended over expandable member 204. Often, the distal portion of outer sheath 208 is preferably formed from metal or a polymer reinforced with a metallic or polymeric braid to resist radial expansion when expandable member 204 is expanded. Outer sheath 208 may further have a liner surrounding its interior of lubricious or low friction material such as PTFE to facilitate relative motion of the outer sheath 208.

Figure 2H:
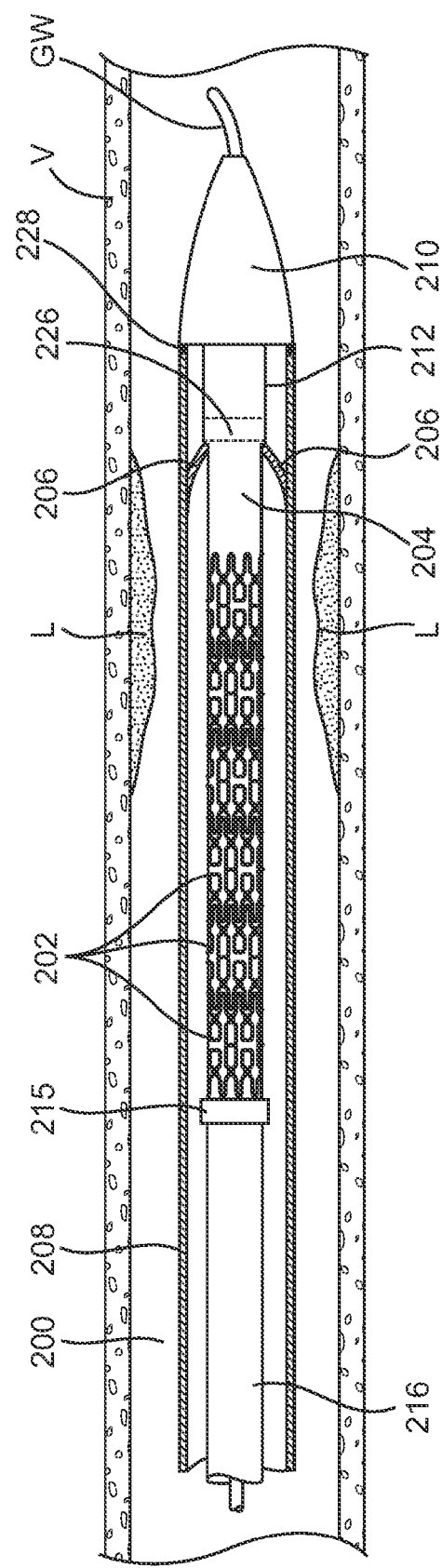
Figure 21:
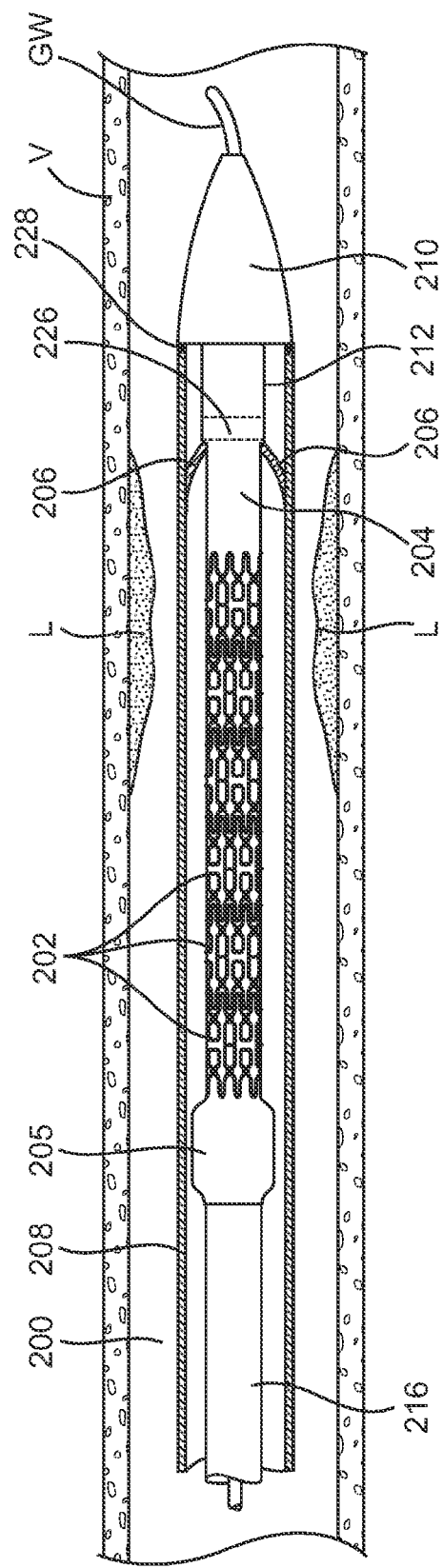
Figure 2J:
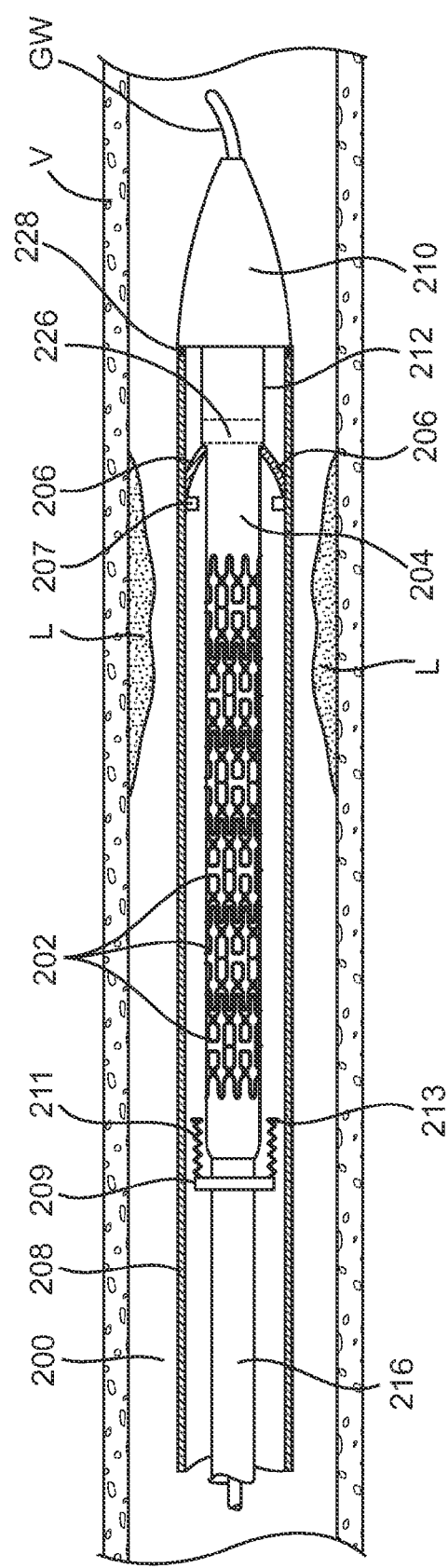

In this embodiment, each prosthetic segment has a length approximately 6 mm long. Thus, in this embodiment, the delivery catheter 200 is adapted to deliver a prosthesis having a length from 6 mm long, up to 36 mm long, in 6 mm increments. Other lengths and quantities of stent segments may be employed and this exemplary embodiment is not meant to limit the scope of the present invention. Stent valve 206 is disposed on the inner diameter of outer sheath 208 and facilitates deployment of stent segments 202 and will be further described below. Pusher tube 214 acts as a backstop element and is engaged with the proximal end of the proximal-most stent segment and prevents the stent segments 202 from being axially displaced in the proximal direction as the outer sheath 208 is retracted. Alternative embodiments of a stent backstop are illustrated in FIGS. 2H-2J. In these embodiments, pusher tube 214 has been eliminated, thus reducing manufacturing cost, facilitating operation and assembly of the device as well as increasing catheter flexibility.

For example, in FIG. 2H, pusher tube 214 has been removed from the delivery catheter and replaced with a hard stop 215 disposed on the catheter shaft 216. The hard stop 215 is typically an annular flange that may be integral with the catheter shaft 216 or the stop 215 may be bonded to the shaft 216. In some embodiments the balloon 204 is bonded to the outer surface of hard stop 215. This prevents stent segments 202 from being retracted proximally over the tapered portion of balloon 204 which forms during inflation. In other embodiments, the hard stop 215 may be attached to the top of the balloon 204 or directly to the catheter shaft 216.

In another alternative embodiment, the balloon itself may provide a stent backstop. In FIG. 2I, a proximal section of balloon 204 has been "pillowed" to create a step 205. This is done typically during the thermoforming process of balloon fabrication. The step is formed either as a result of the excess material of the balloon when folded over the delivery catheter shaft 216 or by partially inflating the balloon during stent delivery. The step is large enough to prevent proximal motion of the stent segments 202. In still another embodiment, FIG. 2J illustrates a stent backstop 209 similar to the stent stop 215 of FIG. 2H with an additional compliant spacer element 211. The stent backstop 209 is a hard stop disposed on the catheter shaft 216. The hard stop 215 is typically an annular flange that may be integral with the catheter shaft 216 or the stop 215 may be bonded to the shaft. The compliant spacer element 211 is retractable in order to allow outer sheath 208 to be withdrawn to engage stent segments 202 more proximally located along the catheter shaft 216 without the backstop 209 and spacer 211 hindering proximal motion of stent valve 206 and outer sheath 208. Flange 207 on the outer sheath engages flange 213 on the spacer 211 during proximal retraction of outer sheath 208, resulting in retraction of spacer 211. Additionally, spacer 211 may be compliant enough to expand with balloon 204 during inflation in the case where all stent segments 202 are deployed.

The length of the lesion to be treated is typically visualized by introducing contrast media into the target vessel V and observing the resulting image under a fluoroscope. Radiopaque markers 226, 228, one at the distal end of the balloon and one at the distal end of the outer sheath 208 may be used to visualize the length of stent segments exposed for deployment relative to the target lesion. This is accomplished by advancing the delivery catheter so that radiopaque marker 226 is at the distal edge of the lesion and then outer sheath 208 is refracted until radiopaque marker 228 is at the proximal edge of the lesion. Retraction of outer sheath 208 selects a number of stent segments 218 to match the length of lesion L and this is depicted in FIG. 2B. Outer sheath 208 is axially retracted in the proximal direction by means of a control mechanism on the proximal end of the delivery catheter 200. As outer sheath 200 is pulled back, the selected number of stent segments 218 is exposed. Pusher tube 214 is operably coupled with outer sheath 208 such that during refraction of the outer sheath 208 to expose stent segments 218, pusher tube 214 remains stationary and acts as a backstop to prevent proximal motion of the stent segments 202, 218 as stent valve 206 passes over them. In FIG. 2B, four segments 218 for a total prosthesis length of 24 mm have been selected to cover an appropriately sized lesion. Additional stent segments 202 may be selected for delivery if the initial quantity exposed is insufficient to cover the target lesion.

Referring now to FIG. 2C, a spacing is created between the stent segments 218 selected for delivery and the segments 202 remaining with the delivery catheter 200. In FIG. 2C, outer sheath 208 is advanced distally with stent valve 206 engaging the proximal-most stent segment 218 in the group selected for deployment. As outer sheath 208 is advanced, stent segments 218 are also advanced distally. Stent segments 218 continue to advance with the outer sheath 208 until the distal most stent 218 is stopped by a stent stop 212. The stent stop 212 is disposed on the inner catheter shaft 216 near the distal end of the balloon 204. Stent stop 212 protrudes radially so as to prevent stent segments 218 from being displaced past the distal end of the balloon 204 and falling off the delivery catheter 200. As outer sheath 208 is advanced stent segments 218 continue to advance distally until they are all grouped together without any spacing between stent segment ends. Additionally, as previously mentioned, balloon 204 is often attached to the outer surface of stopping member 212. This prevents stent segments 202 from being advanced distally over the tapered portion of balloon 204 which forms during inflation, and thus ensures uniform expansion of stent segments 202 during deployment. Furthermore, the distal motion of the stent segments 218 selected for deployment, creates a spacing between those segments and any remaining stent segments 202. This spacing allows a proper balloon taper to be formed between the two groups 202, 218 of segments and is needed for balloon inflation. The spacing is typically 0.5 mm to 5 mm.

In FIG. 2D, the outer sheath 208 is retracted proximally so that the selected stent segments 218 are no longer constrained from expansion while still covering the stent segments 202 not selected for delivery. Outer sheath 208 is retracted sufficiently so that the spacing previously created between the group of stent segments 218 selected for delivery and those remaining is unconstrained, in order to permit proper balloon expansion. During retraction of the outer sheath 208, pusher tube 214 again acts as a backstop to prevent displacement of the remaining stent segments 202.

Referring now to FIG. 2E, the selected stent segments 218 are deployed. Expandable member 204, typically a balloon, is inflated with a fluid such as contrast media and/or saline to achieve an expanded diameter 220. Radial expansion of expandable member 220 correspondingly expands stent segments 218 against the vessel wall across lesion L. Outer sheath 208 and radiopaque marker 226 constrain a proximal portion of inflatable member 204 and prevents deployment of the stent segments 202 remaining with the delivery catheter 200. After stent segments 218 are deployed, expanded member 220 is deflated and removed from the deployed stent segments 218, leaving stent segments 218 in a plastically deformed, expanded configuration in the vessel V, at the site of the lesion, L. This is illustrated in FIG. 2F. Stent segments 202 remain with the delivery catheter 200 and then both are removed and retracted from the vessel V.

FIGS. 3A-3E illustrate the deployment of selected prosthetic segments to treat a lesion in another embodiment. In this exemplary embodiment, the prosthetic segments have a gap or spacing between segment ends. As discussed above, this embodiment will be described in the context of a coronary artery stent procedure, but this is not intended to limit the invention which may be employed in any variety of blood vessels and other body lumens in which stents or tubular prostheses are deployed.

The embodiment shown in FIGS. 3A-3E is similar to that previously discussed, however there are differences. As previously mentioned, here, prosthetic segments 302 have a gap or spacing between segment ends. The spacing between segment ends is typically 0.5 mm to 1 mm, so as to minimize shortening of the final prosthesis length. The spacing is advantageous because it allows stent valve or separator 306 to more easily engage the stent segment ends by providing a raised ledge that is easy to push against. This embodiment also has a stopping member 312 that is similar to stopping member 212 in FIGS. 2A-2G above, and is typically an annular flange extending radially outward to prevent displacement of the prosthetic segments 302 beyond the stopping member 312.

Similar to the procedure discussed above, a guide catheter (not illustrated) is first inserted into a peripheral artery such as the femoral artery, typically using a percutaneous procedure such as the Seldinger technique or by surgical cutdown, and then advanced to the ostium of the right or left coronary artery. Guidewire GW is then inserted through the guiding catheter and advanced to the target vessel V where a lesion L to be treated is located. The proximal end of guidewire GW is then inserted through nosecone 310 and guidewire tube 122 (seen in FIG. 1) which is outside the patient's body.

FIG. 3A shows stent delivery catheter 300 slidably advanced over the guidewire GW into the vessel V so that the nosecone 310 is distal to the lesion L. Stent segments 302 having a spacing between ends are disposed over expandable member 304 and covered by outer sheath 308. The segments 302 are positioned over balloon 304 leaving a distal portion of the balloon 304 free of any prosthetic segments 302. This uncovered region is necessary so that prosthetic segments 302 selected for delivery may be advanced distally during their deployment. A stopping member 312 disposed near the distal end of inner shaft 316 prevents the stent segments from being advanced too far distally which could result in the prosthetic segments 302 falling off of the delivery catheter 300. The stopping member 312 in this embodiment is an annular flange either disposed on the outer shaft 316 or a part of the nose cone 310. Often balloon 304 is attached to the outer surface of stopping member 312. This prevents stent segments 302 from being advanced distally over the tapered portion of balloon 304 which forms during inflation, and thus ensures uniform expansion of stent segments 302 during deployment. Additional details on stent stop 312 may be found in U.S. patent application Ser. No. 10/884,616 which has previously been incorporated by reference.

In this embodiment, four stent segments 302 are disposed on the stent delivery catheter 300, each having a length approximately 6 mm long. Thus, in this embodiment, the delivery catheter 300 is adapted to deliver a prosthesis from 6 mm long, up to 24 mm long, in 6 mm increments. Other lengths and quantities of stent segments may be employed and this exemplary embodiment is not meant to limit the scope of the present invention. Stent valve 306 is disposed on the inner diameter of outer sheath 308 and facilitates deployment of stent segments 302. A pusher tube 314 axially disposed along the catheter body 316 may be optionally employed in this embodiment to limit proximal axial motion of stent segments 302 during retraction of outer sheath 308. Alternatively, the pusher tube 314 may be eliminated and alternative backstops such as those previously described (e.g. FIGS. 2H-2J) may be employed.

The length of the lesion to be treated is typically visualized by introducing contrast media into the target vessel V and observing the resulting image under fluoroscopy. Radiopaque markers 326, 328, one at the distal end of the balloon 304 and one at the distal end of the sheath 308 may be used to visualize the length of stent segments exposed for deployment relative to the target lesion. This is achieved by advancing the delivery catheter 300 so that radiopaque marker 326 is at the distal edge of the lesion and then outer sheath 308 is retracted until radiopaque marker 328 is at the proximal edge of the lesion. Retraction of outer sheath 308 selects a number of stent segments 318 to match the length of lesion L and this is depicted in FIG. 3B. Outer sheath 308 is axially retracted in the proximal direction by means of a control mechanism on the proximal end of the delivery catheter 300. As outer sheath 308 is pulled back proximally, the selected number of stent segments 318 are exposed. Pusher tube 314 is operably coupled with outer sheath 308 such that during refraction of outer sheath 308 to expose stent segments 318, the pusher tube 314 remains stationary and serves as a backstop to prevent proximal motion of the proximal-most stent segment 302 as the stent valve 306 passes over them. Proximal motion of the other stent segments is also eventually hindered once the line of stent segments butt up against the proximal-most stent segment. In FIG. 3B, three segments 318 have been selected to cover a lesion approximately 18 mm long. Additional stent segments 302 may be added to the group selected for delivery if initial quantity exposed is insufficient to cover the target lesion.

Referring now to FIG. 3C, the selected stent segments 318 are advanced distally until their motion is prevented by stopping member 312. Advancement is accomplished by advancing outer sheath 308 distally. As the outer sheath 308 is moved distally, stent valve 306 engages the proximal-most stent segment end. Stent segments 302 have a space between their ends and this allows the stent valve 306 to engage the segment end and push against it. Stopping member 312 prevents stent segments 318 from being advanced distally off of the delivery catheter 300. The stopping member 312 is typically an annular flange that extends radially outward to prevent displacement of the prosthetic segments 318. Often, balloon 304 is attached to the outer surface of stopping member 312. This prevents stent segments 318 from being advanced distally over the tapered portion of balloon 304 which forms during inflation, and thus ensures uniform expansion of stent segments 318 during deployment. Additionally, once the stent segments 318 have been advanced distally, they are disposed end-to-end in engagement with one another, without intervening gaps.

In FIG. 3D, outer sheath 308 is again retracted proximally away from the stent segments 318 selected for delivery so they are no longer constrained from expansion, while still covering the stent segments 302 which have not been selected for delivery. Outer sheath 308 is retracted sufficiently so that the spacing previously created between the group of stent segments 318 selected for delivery and those remaining 302 is unconstrained, in order to permit proper balloon expansion. Again, pusher tube 314 is used as a backstop to prevent proximal displacement of the remaining stent segments 302.

Figure 3E:
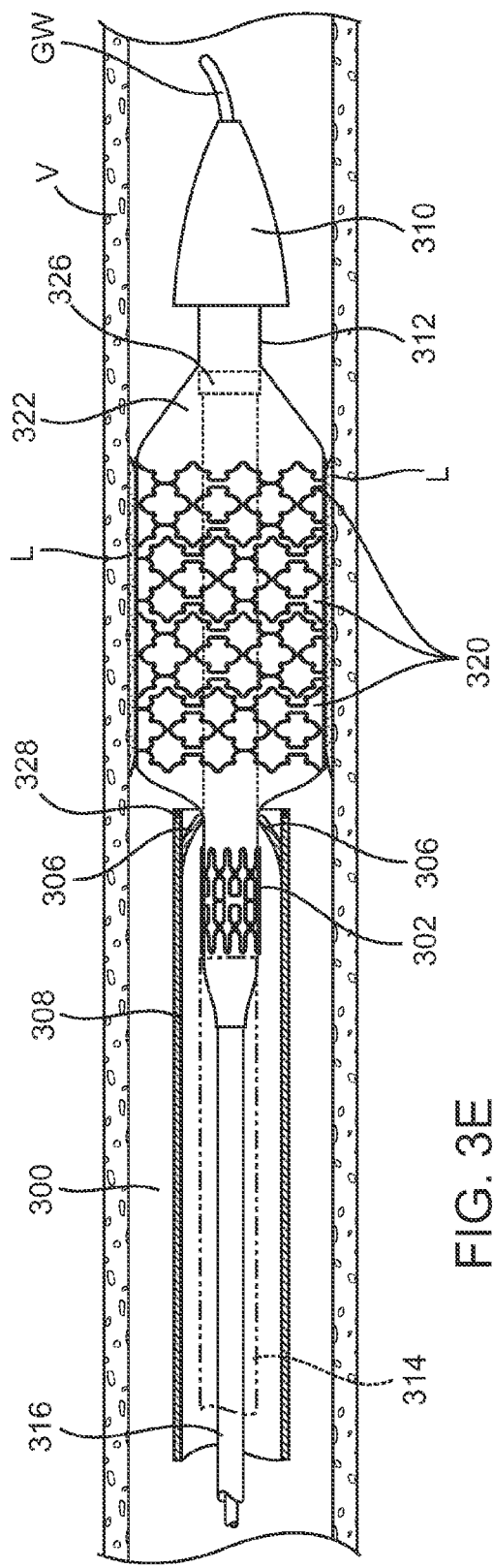

Referring now to FIG. 3E, the selected stent segments 318 are deployed. Expandable member 304, typically a balloon, is inflated with a fluid such as contrast media and/or saline to achieve an expanded diameter 322. Radial expansion of expandable member 322 correspondingly expands stent segments 318 to a larger diameter 320 against the vessel wall across lesion L. Outer sheath 308 constrains the proximal portion of inflatable member 304 and prevents deployment of the stent segments 302 remaining with the delivery catheter 300. After stent segments 320 are deployed, expanded member 322 is deflated and removed from the deployed stent segments 320, leaving stent segments 320 in a plastically deformed, expanded configuration in the vessel V, at the site of the lesion, L. Stent segments 302 remain with the delivery catheter 300 and then both are removed and refracted from the vessel V.

Another embodiment illustrating the deployment of selected prosthetic segments to treat a lesion is illustrated in FIGS. 4A-4D. This exemplary embodiment is described in the context of a coronary artery stenting procedure, but is not intended to limit the invention which may be employed in any variety of other body lumens and blood vessels where stents and tubular prostheses are deployed. While similar to the embodiment previously discussed, there are differences. As in the previous embodiment, the prosthetic segments 402 have a gap or spacing between segment ends. This gap is typically 0.5 mm to 1 mm and is advantageous because it allows stent valve or separator 406 easily engage the ends of stent segments 402 by providing a raised ledge that is easy to push against. The embodiment illustrated in FIGS. 4A-4D also has a stent stopping member 412 that comprises an annular flange disposed on inner shaft 416 or that may be formed as a part of the nose cone 410. The annular flange has a diameter sufficient to provide a stopping edge that prevents stent segments 402 from moving distally past the stopping member 412. Balloon 404 is often attached to the outer surface of stopping member 412. This prevents stent segments 402 from being advanced distally over the tapered portion of balloon 404 which forms during inflation, and thus ensures uniform expansion of stent segments 202 during deployment.

Additionally, in this embodiment, an elastomeric separator or stent valve 406 is used. The separator 406 is a resilient elastomeric member disposed on the distal end of outer sheath 408. The separator is adapted to engage the end of a stent segment 402 exposed in the gap region between segments 402. Thus, when the stent valve engages a prosthetic segment 402, the segment 402 may be advanced distally as the stent valve 406 and outer sheath 408 are advanced. The stent valve 406 is also adapted such that as the stent valve 406 is retracted proximally over the stent segments 402, the valve 406 will slide over the stent segments 402 without displacing them.

Another advantage of this embodiment includes the flexible nature of the stent valve 406. Stent valve 406 may be fabricated from an elastomeric material such as silicone, latex, urethane or the like that is sufficiently flexible to be deflected outwardly during inflation of balloon 404. Additionally, the inside diameter of the valve may be coated with a lubricious material such as PTFE to reduce the force required to retract the sheath. The valve leaflets are long enough to allow formation of a proper balloon taper during inflation of balloon 404. Thus, an automatic spacing is created by the stent valve 406 between the distal end of outer sheath 408 and the proximal-most end of the stent segments 418 selected for delivery because the stent valve expands with balloon 404. This spacing is typically about 0.5 mm to 5 mm.

In FIGS. 4A-4D access to the vessel is similar to the procedures previously described. A guide catheter (not illustrated) is first inserted into a peripheral artery such as the femoral artery, typically using a percutaneous procedure such as the Seldinger technique or by surgical cutdown, and then advanced to the ostium of the right or left coronary artery. Guidewire GW is then inserted through the guiding catheter and advanced into the target vessel V where a lesion L to be treated is located. The proximal end of guidewire GW is then inserted through nosecone 410 and guidewire tube 122 (seen in FIG. 1) which is outside the patient's body.

Figure 4A:
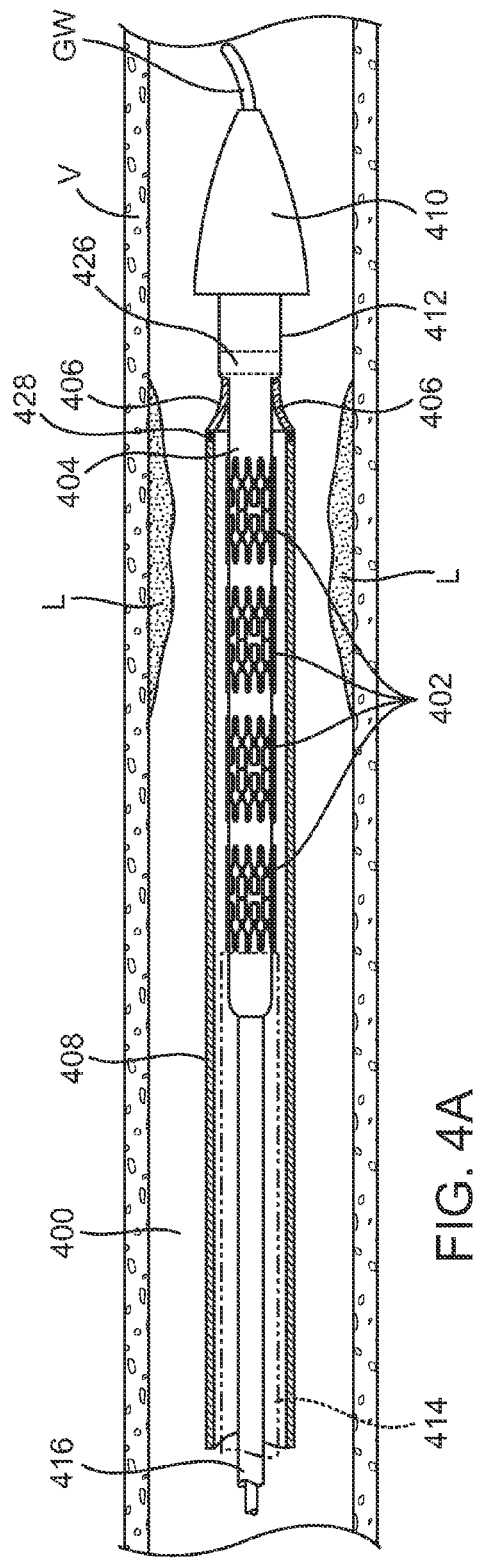
FIGS. 4A-4D illustrate selection and deployment of prosthetic stent segments in accordance with still another exemplary embodiment.

FIG. 4A shows stent delivery catheter 400 slidably advanced over the guidewire GW into the vessel V so that the nosecone 410 is distal to the lesion L. Stent segments 402 having a spacing between ends are disposed over expandable member 404 and covered by outer sheath 408. The spacing is typically between 0.5 mm and 1 mm. In this embodiment, four stent segments 402 are disposed on the stent delivery catheter 400, each having a length approximately 6 mm long. Thus, in this embodiment, the delivery catheter 400 is adapted to deliver a prosthesis having a length from about 6 mm long, up to 24 mm long, in 6 mm increments. Other lengths and quantities of stent segments may be employed and this exemplary embodiment is not meant to limit the scope of the present invention. Stent valve 406 is disposed on the inner diameter of outer sheath 408 and facilitates deployment of stent segments 402. A pusher tube 414 axially disposed along the catheter body 416 may be employed in this embodiment to limit proximal axial motion of the proximal-most stent segment 402 and the other stent segments as they bunch up together, during retraction of outer sheath 408. Additionally, the pusher tube 414 may be eliminated and other backstops employed, such as those previously described in FIGS. 2H-2J.

A stopping member 412 disposed near the distal end of balloon 404 prevents the stent segments 402 from being advanced too far distally which could result in the prosthetic segments 402 falling off of the delivery catheter 400. The stopping member 412 is similar to stopping member 212 in FIGS. 2A-2G and is typically an annular flange that extends radially outward to prevent displacement of the prosthetic segments 402 beyond the stopping member 412. Often, balloon 404 is attached to the outer surface of stopping member 412. This prevents stent segments 402 from being advanced distally over the tapered portion of balloon 404 which forms during inflation, and thus ensures uniform expansion of stent segments 402 during deployment. Additional details on stent stop 412 may be found in U.S. patent application Ser. No. 10/884,616 which has previously been incorporated by reference.

Figure 4B:
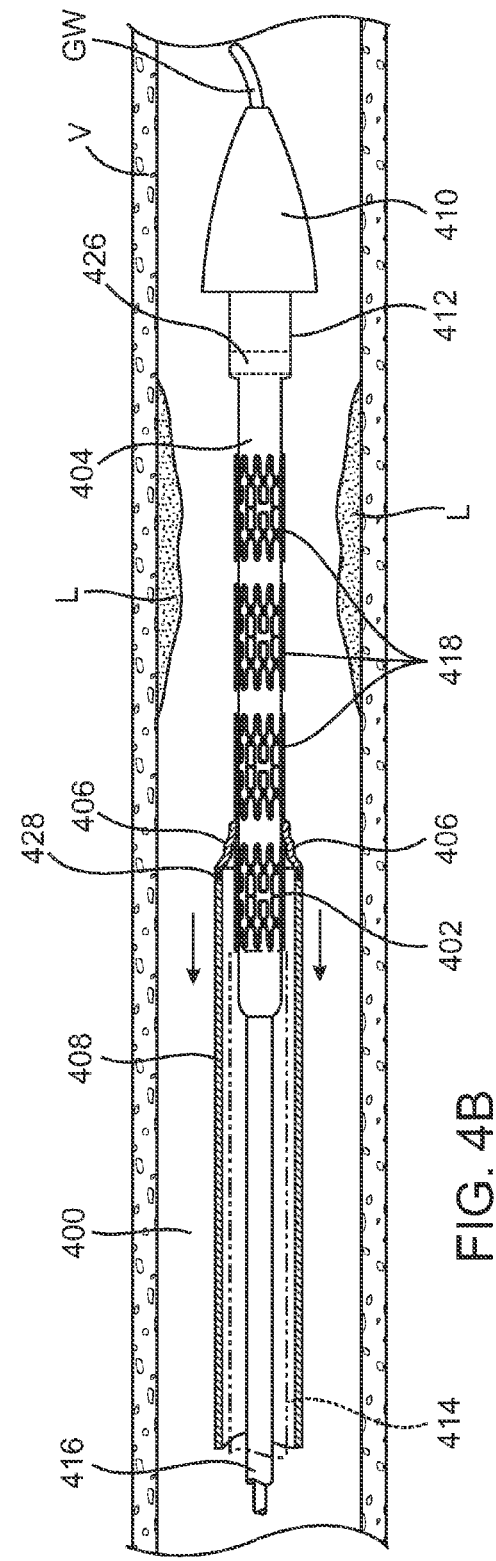

The length of the lesion to be treated is typically visualized by introducing contrast media into the target vessel V and observing the resulting image under fluoroscopy. Radiopaque markers 426, 428, one at the distal end of the balloon 404 and one at the distal end of outer sheath 408 may be used to visualize the length of stent segments exposed for deployment relative to the target lesion. This is achieved by advancing the delivery catheter 400 so that radiopaque marker 426 is at the distal edge of the lesion and outer sheath 408 is retracted until radiopaque marker 428 is at the proximal edge of the lesion. Retraction of outer sheath 408 selects a number of stent segments 418 to match the length of lesion L and this is depicted in FIG. 4B. Outer sheath 408 is axially retracted in the proximal direction by means of a control mechanism on the proximal end of the delivery catheter 400. As outer sheath 408 is pulled back proximally, the selected number of stent segments 418 is exposed. Pusher tube 414 is operably coupled with outer sheath 408 such that during refraction of outer sheath 408 to expose stent segments 418, the pusher tube 414 remains stationary and serves as a backstop to prevent proximal motion of the stent segments 402, 418 as the stent valve 406 passes over them. In FIG. 4B, three prosthetic segments 418 have been selected to cover a lesion approximately 18 mm long. Additional stent segments 402 may be added to the group selected for delivery if the initial quantity exposed is insufficient to cover the target lesion.

Figure 4C:
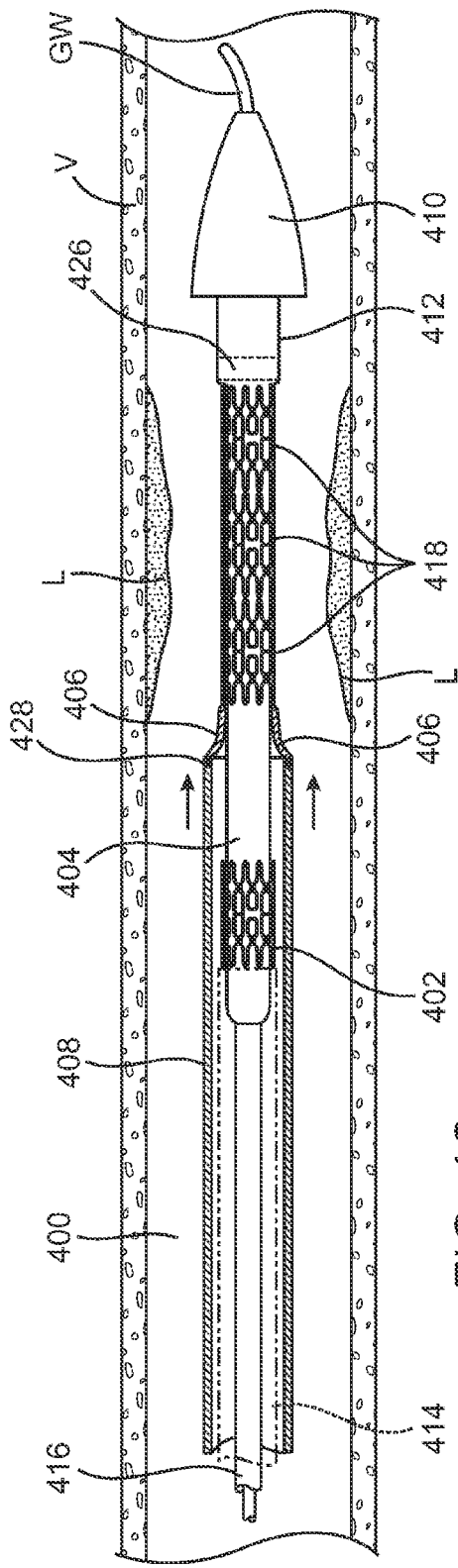

Referring now to FIG. 4C, the selected stent segments 418 are advanced distally until their motion is prevented by a stopping member 412, which is typically an annular flange extending radially outward. This is accomplished by advancing outer sheath 408 distally. Stent segments 402 have a space between their ends and this allows stent valve 406 on outer sheath 408 to engage the proximal-most stent segment 418 end. Stopping member 412 prevents stents segments 418 from being advanced distally off of the delivery catheter 400 and often, balloon 404 is attached to the outer surface of stopping member 412. This prevents stent segments 402 from being advanced distally over the tapered portion of balloon 404 which forms during inflation, and thus ensures uniform expansion of stent segments 402 during deployment. Additionally, once the stent segments 418 have been advanced distally, they are disposed end-to-end in engagement with one another, without intervening gaps.

Unlike previous embodiments, further retraction of outer sheath 408 to create a spacing between the distal end of outer sheath 408 and the proximal-most end of the stent segments 418 selected for delivery is not required. Stent valve 406 is designed not only to frictionally engage and move stent segments 418, but the stent valve 406 is also adapted to expand under the pressure of balloon 404 when it is inflated. It therefore automatically creates the spacing necessary by expanding with the balloon 404.

Figure 4D:
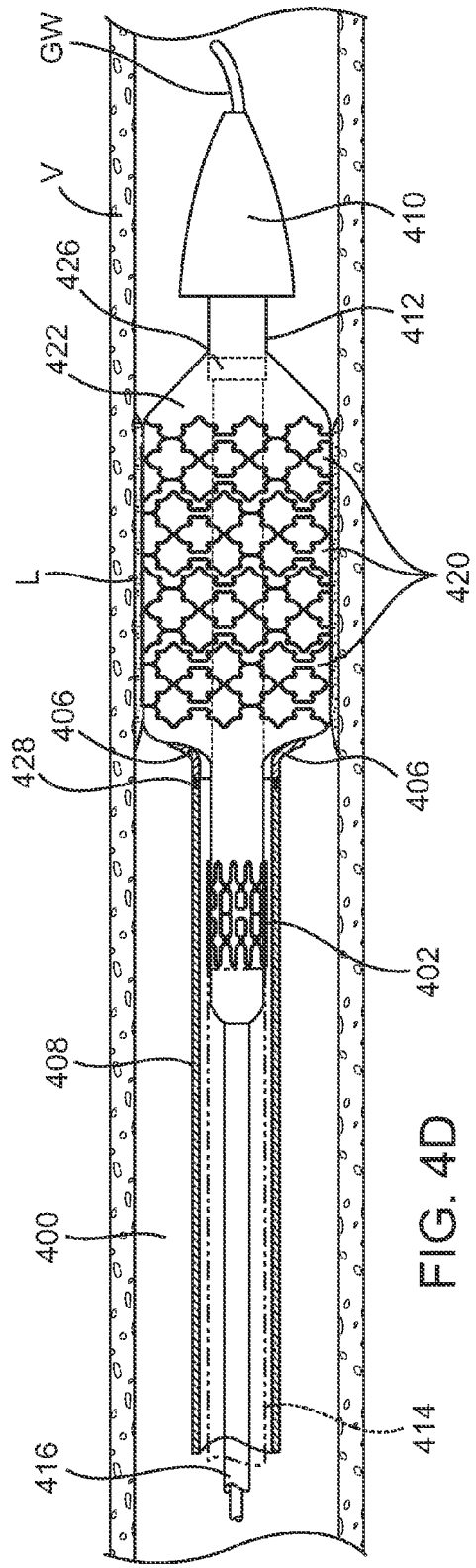

Referring now to FIG. 4D, the selected stent segments 418 are deployed. Expandable member 404, typically a balloon, is inflated with a fluid such as contrast media and/or saline to achieve an expanded diameter 422. Radial expansion of expandable member 422 correspondingly expands stent segments 418 to a larger diameter 420 outward against the vessel wall across lesion L. Outer sheath 408 and radiopaque marker 428 constrain inflatable member 404 and prevents deployment of the stent segments 402 remaining with the delivery catheter 400. Stent valve 406 is engaged by inflatable member 404 and is deflected radially outward as the inflatable member expands. After stent segments 420 are deployed, expanded member 422 is deflated and removed from the deployed stent segments 420, leaving stent segments 420 in a plastically deformed, expanded configuration in the vessel V, at the site of the lesion, L. Stent segments 402 remain with the delivery catheter 400 and then both are removed and retracted from the vessel V.

Figure 5A:
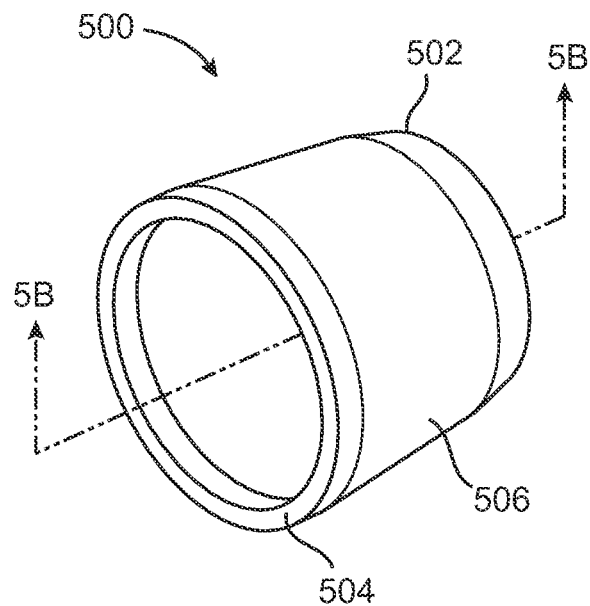
FIGS. 5A and 5B show a perspective and a cross-sectional view of one exemplary embodiment of a stent valve.
Figure 5B:
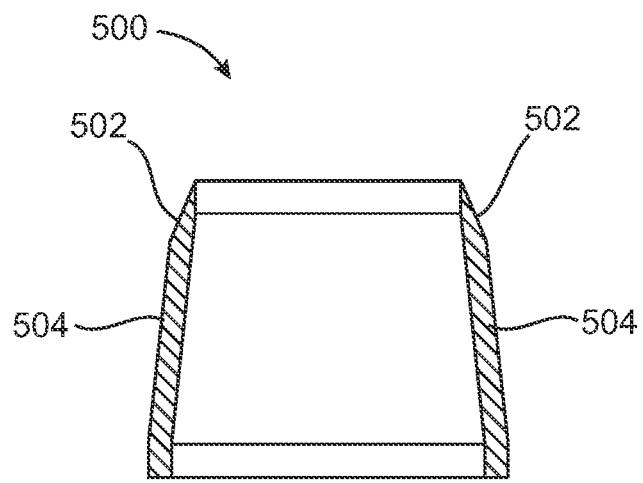

FIGS. 5A-13 illustrate several embodiments of stent valves that can be used in the delivery catheter embodiments previously described. In FIG. 5A, a polymeric valve concept is shown. Stent valve 500 comprises a thin walled cylinder or tube 504 molded from a thermoplastic or a thermoplastic elastomer (TPE) or a thermoset such as silicone. The outer diameter of the cylinder is tapered and has a beveled distal tip 502. In this embodiment, stent valve 500 is joined at an outer section 506 with or embedded in an outer sheath and can be used in delivery catheters where the stent segments are adjacent or spaced apart. The thin flat beveled section minimizes the force exerted on stent segments as the valve is refracted over the segments. When the sheath is advanced over stent segments having interleaved ends in engagement with one another, the thin section buckles and engages the outside diameter of the appropriate segment so that is can be advanced distally. Alternatively, in the spaced stent segment embodiment, the thin flat beveled section 502 on the distal end of the valve 500 is able to fit into the gaps between stent segments and engage a stent segment end as an outer sheath is advanced distally, which correspondingly advances stent segments distally. The stent valve 500 is sufficiently compliant at the thin flat beveled section 502 so that as the stent valve 500 is retracted proximally over a stent segment, the valve can resiliently expand to slide over the stent segment without moving it. A pusher tube may also be used as described above to prevent proximal motion of stent segments. In preferred embodiments, the stent valve 500 may be fabricated from silicone, latex, urethane or other similar elastomeric materials and polymers. The outer diameter of the cylinder is no larger than the outer diameter of the prosthetic segment outer diameter so that the stent valve 500 engages the stent segment end when unstretched. FIG. 5B is a cross-sectional view of stent valve 500, taken along line 5B-5B.

Figure 6A:
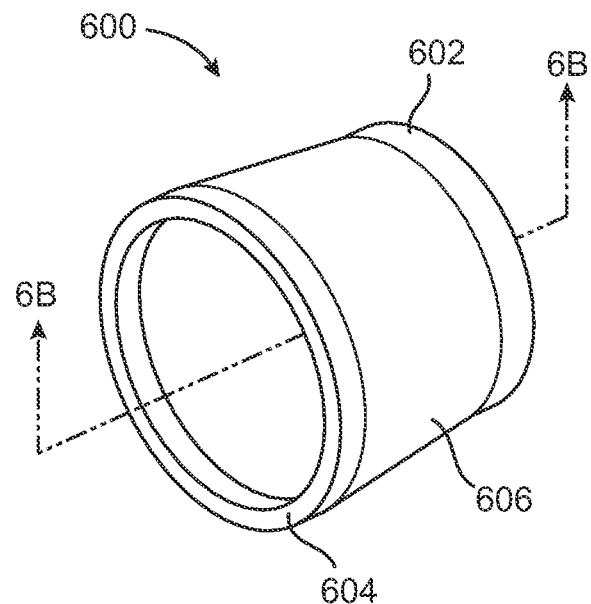
FIGS. 6A and 6B show a perspective and a cross-sectional view of another exemplary embodiment of a stent valve.
Figure 6B:
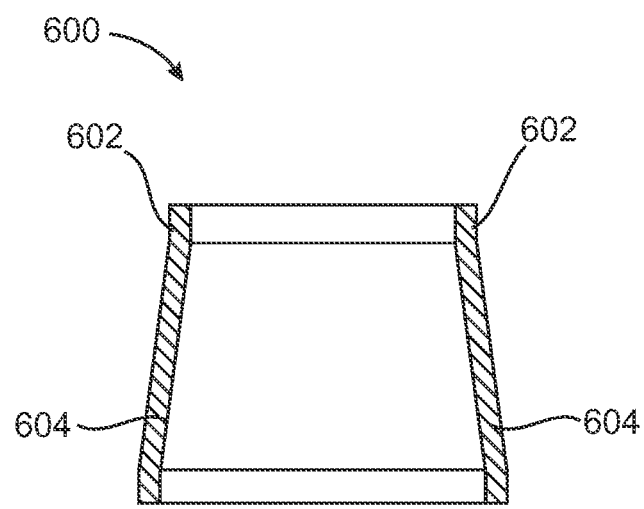

FIGS. 6A and 6B show an alternative embodiment of a thin walled polymeric stent valve or separator molded from a thermoplastic or TPE. Exemplary materials include but are not limited to latex, silicone, urethane and the like. In FIG. 6A, stent valve 600 is a thin walled cylinder or tube with a tapered outer diameter and a blunt end 602 that acts as a bumper when engaged with a stent segment end when the valve 600 is unstretched. The outer diameter of stent valve 600 is no larger than the outer diameter of the prosthetic segment diameter so that the stent valve 600 engages the stent segment ends when unstretched. This embodiment is preferably used in a delivery catheter where stent segments are spaced apart, but could also be employed when the stent segment ends are interleaved in engagement with one another. Stent valve 600 may be attached along its exterior 606 to an outer sheath or embedded in the distal tip of the sheath in a stent delivery catheter. When the outer sheath is advanced distally forward, so too is stent valve 600. As the stent valve passes over stent segments, the blunt end 602 catches a stent segment end spaced apart from another stent segment and pushes the stent segment distally. Refraction of the outer sheath and stent valve 600 in the proximal direction does not move the stent segment due to the resilient nature of stent valve 600 which expands and slides over the stent segments when moved in the proximal motion. An additional pusher tube may also be used to prevent proximal motion of stent segments, as previously described above. FIG. 6B is a cross-sectional view of stent valve 600 taken along line 6B-6B.

Figure 7A:
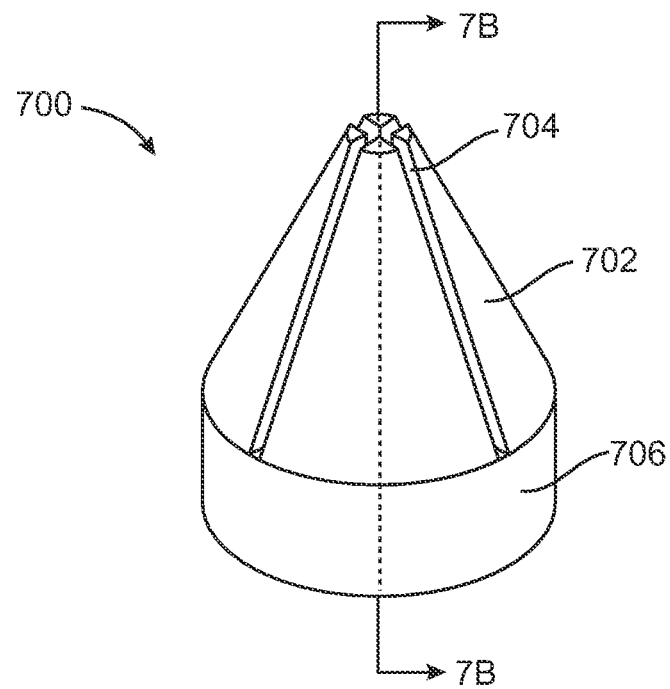
FIGS. 7A and 7B show a perspective and a cross-sectional view of yet another exemplary embodiment of a stent valve.
Figure 7B:
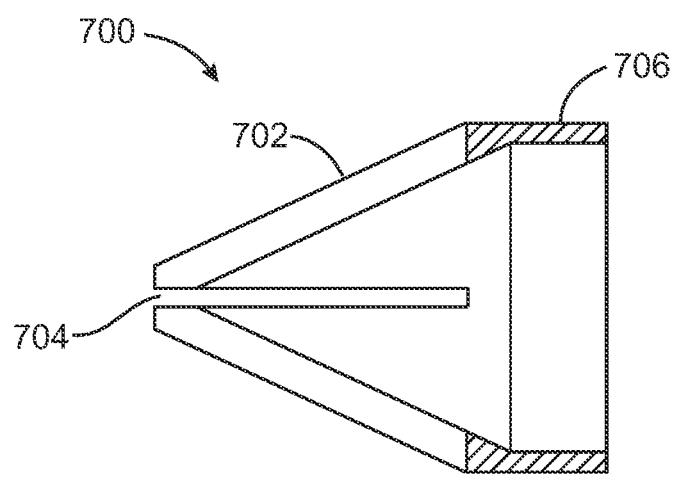

FIGS. 7A-7B show a conically shaped stent valve embodiment. The stent valve 700 in FIG. 7A is also a thin walled valve molded from a resilient thermoplastic or TPE. The stent valve 700 has slits 704 along a tapered portion 702 which allow each section of tapered portion 702 to radially deflect and pass over stent segments in the proximal direction and resiliently return to a conical shape as valve 700 is advanced distally. As in other embodiments, stent valve 700 may be attached to or embedded in an outer sheath along an exterior surface 706 of the valve 700. Stent valve 700 is designed to be used in stent delivery catheters having stents spaced apart or the stents may having interleaving ends in engagement with one another. That way, as the stent valve 700 is advanced distally, the valve can easily engage stent segment ends that are spaced apart and push the segments distally. A pusher tube may be employed in the delivery catheter to serve as a backstop to help prevent proximal stent segment motion and this has previously been discussed. FIG. 7B is a cross-sectional view of stent valve 700 taken along line 7A-7A.

Figure 8A:
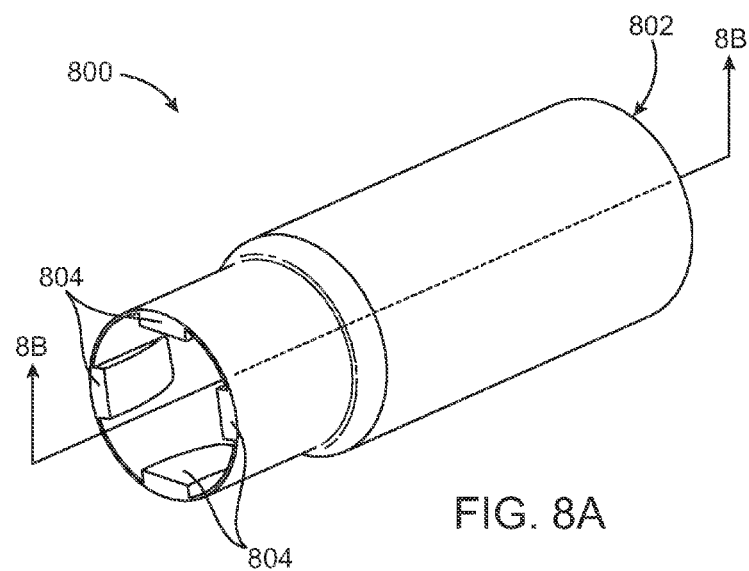
FIGS. 8A and 8B show a perspective and cross-sectional view of still another exemplary embodiment of a stent valve.
Figure 8B:
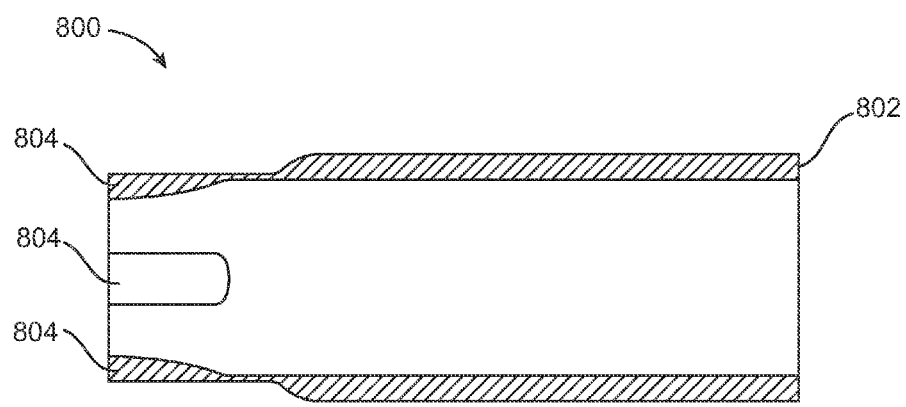

FIGS. 8A-8B show yet another molded stent valve embodiment. In this embodiment, the stent valve 800 is formed from a resilient thermoplastic and is thermally bonded at one end 802 to, or embedded in the distal end of an outer sheath. The stent valve has small tabs 804 with blunt distal ends that engage the struts of spaced stent segments as the outer sheath is moved distally forward. The ramped shape of the tabs 804 also allow the stent valve to disengage from the stent struts when the outer sheath is moved in the proximal direction. A cross-sectional view taken along line 8B-8B is shown in FIG. 8B.

Figure 9A:
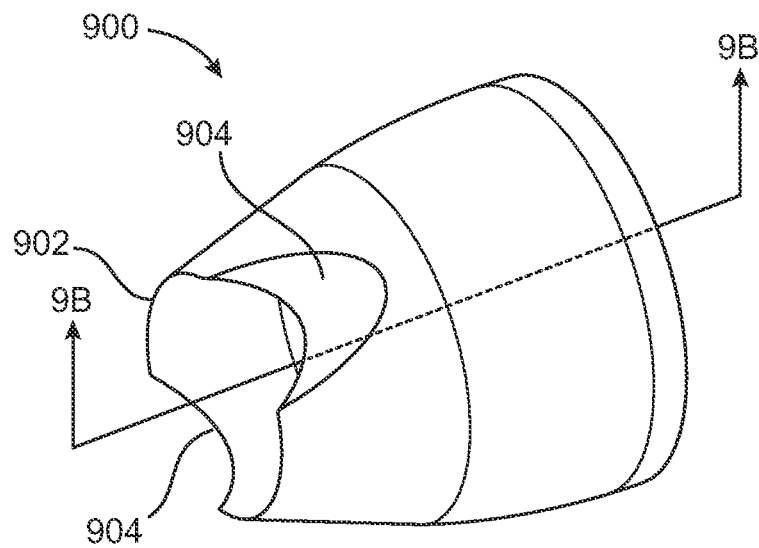
FIGS. 9A and 9B show a perspective and a cross-sectional view of another exemplary embodiment of a stent valve.
Figure 9B:
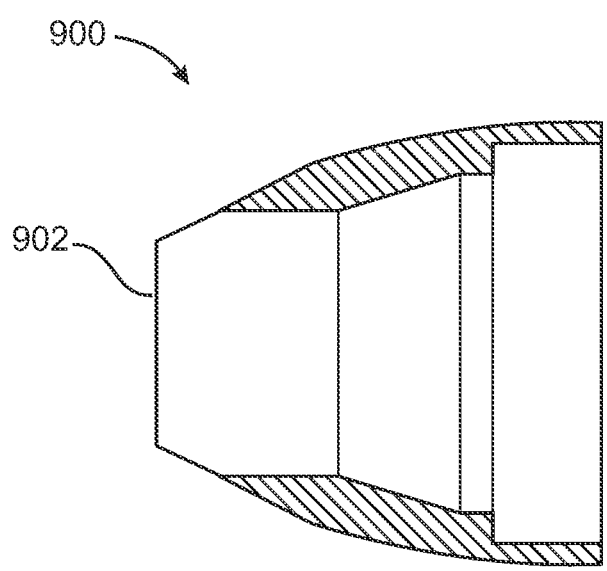

Another polymeric stent valve embodiment is illustrated in FIGS. 9A-9B. Here, in FIG. 9A a stent valve 900 is molded or formed from a resilient thermoplastic and thermally bonded to the distal end of an outer sheath or embedded within the sheath. The edges 902 of this stent valve 900 are cut or molded so that the leading edge is sharp like a knife edge. The purpose of these edges 902 is to engage stent segment ends as the valve 900 is advanced distally forward when stent segments have interleaved ends in engagement with one another. Meanwhile, thin scalloped like portions 904 of the stent valve 900 allow the knife edges 902 to flex and thus as the stent valve is retracted proximally over stent segments, the valve expands and slides over the stents without moving the segments. FIG. 9B is a cross-sectional view of the stent valve 900 taken along line 9B-9B.

Figure 10A:
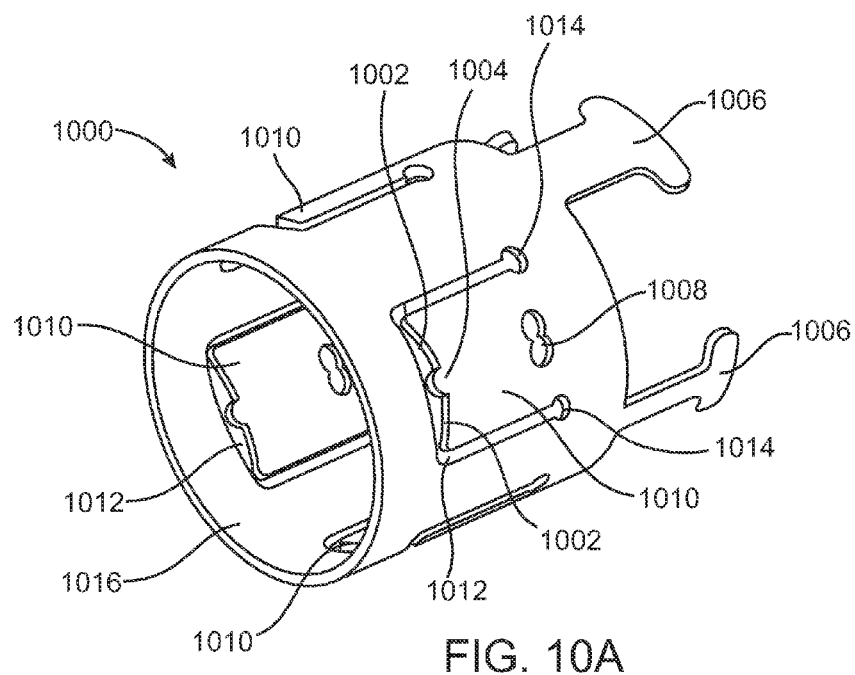
FIGS. 10A and 10B show a perspective and an unrolled, flattened view of yet another exemplary embodiment of a stent valve.
Figure 10B:
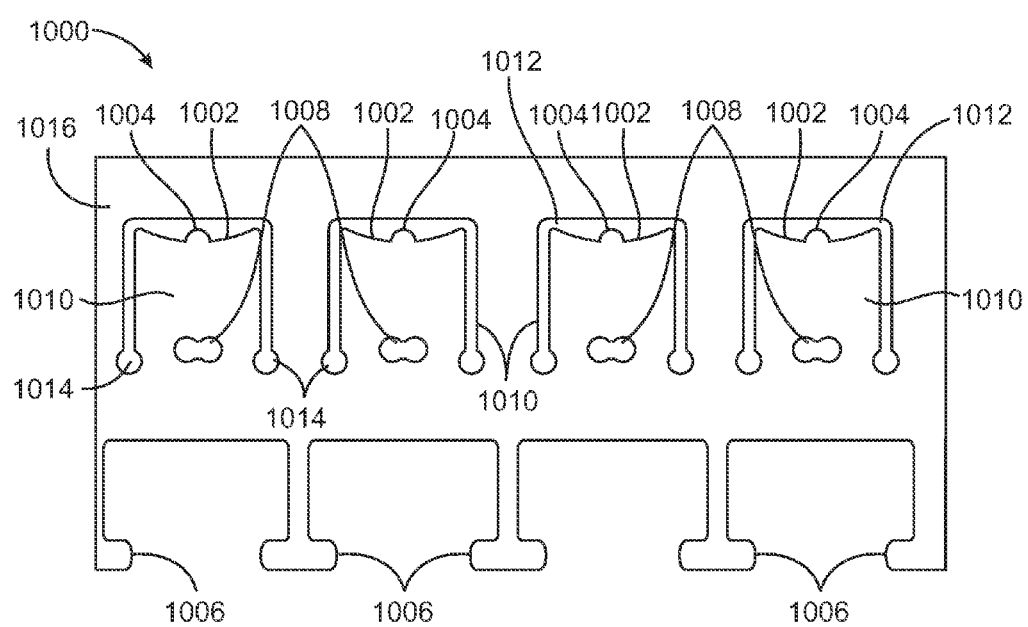

FIGS. 10A-13 illustrate several embodiments of stent valves that are preferably fabricated from flexible metals such as nitinol or spring temper stainless steel, although thermoplastics may also be employed in their construction. In FIG. 10A, a stent valve 1000 comprises a series of four fingers 1010 spaced approximately 90° apart. The distal end of each finger 1010 has a concave radius 1002 which matches the radius of the stent segments that the valve 1000 is designed to capture, thereby creating a greater contact area. Additionally, a semicircular tab 1004 is disposed on each finger. The semicircular tab 1004 and concave radius 1002 help each finger 1010 to engage a stent segment and move it in the distal direction, without damaging the surface of the prosthetic segments, any therapeutic coating carried on the prosthetic segments or the expandable member. Also, each finger 1010 is bent radially inward at a slight angle and distally inclined so that the finger will engage with a stent segment as the valve is moved in the distal direction and slide over the segments as the valve is moved in the proximal direction. Circular cutouts 1014 serve as strain reliefs to distribute forces from fingers 1010 to prevent fatigue or fracture of the fingers 1010. Also, the size of the circular cutouts 1014 can be varied to provide resiliency and vary the amount of pressure which fingers 1010 apply to the prosthetic segments. Additional cutouts 1008 at the proximal end of each finger 1010 act as hinges and help the finger 1010 flex as it moves inwardly and outwardly. Attachment members 1006 on the proximal end of the stent valve 1000 help join the stent valve 1000 with the distal end of an outer sheath or alternatively, the stent valve 1000 can be embedded within a distal portion of the outer sheath. FIG. 10B shows a two-dimensional version of stent valve 1000 after it has been flattened and unrolled. The stent valve 1000 may be laser cut, EDM machined or photoetched from either flat stock or tubing made from nitinol, spring temper stainless steel or the like.

Figure 11A:
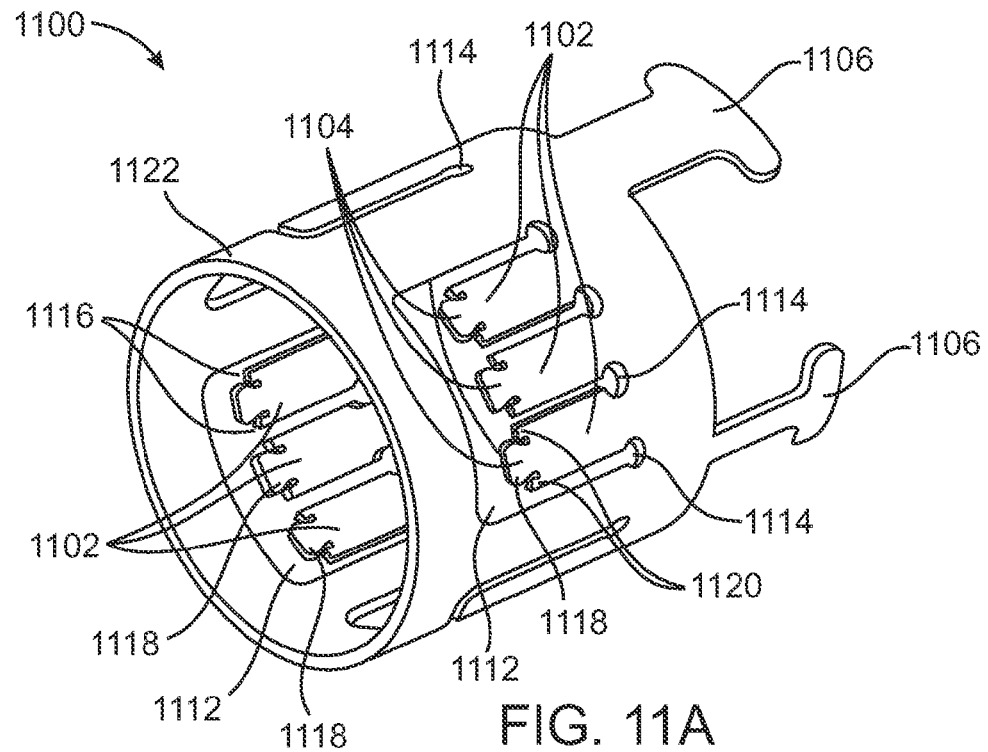
FIGS. 11A and 11B show a perspective and an unrolled, flattened view of still another exemplary embodiment of a stent valve.
Figure 11B:
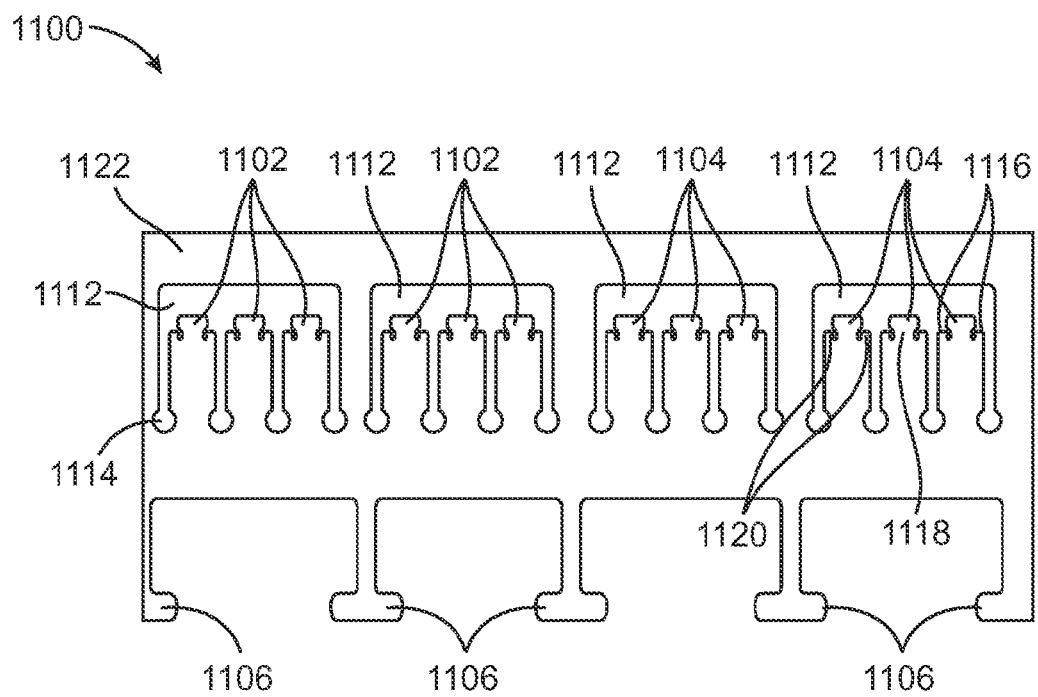

FIGS. 11A and 11B show an alternative embodiment of a stent valve. In FIG. 11A, stent valve 1100 has a plurality of one-way grip structures 1112 formed thereon. Each one-way grip structure 1112 includes several resilient tabs or fingers 1102, which are angled inward and distally inclined to engage prosthetic segments. Tabs 1102 include a repeating pattern of three adjacent fingers. Each tab 1102 also includes a rounded end 1104 that helps avoid damaging coatings on the stent segments. Circular cutouts 1114 are strain reliefs that help prevent tearing or fracture of the tab 1102. Also, the cross-sectional size of circular cutouts 1114 can be varied to provide resiliency and vary the pressure which tabs 1102 apply to the stent segments. Recesses 1116 can be provided on either side of rounded ends 1118 so as to define a pair of tips 1120 along the lateral sides of the tabs 1104. Tips 1120 are adapted to engage the stent segments so as to keep rounded ends 1118 from digging into the balloon or expandable member as the stent valve 1100 is advanced distally relative to the expandable member. Engagement tabs 1106 help connect the stent valve 1100 with the distal end of an outer sheath, or alternatively, the stent valve 1100 may be embedded within a distal portion of the outer sheath. FIG. 11B is a two-dimensional version of stent valve 1100 after it has been flattened and unrolled. The stent valve 1100 may be manufactured similarly to the previous embodiment such as by be laser cutting, EDM machining or photoetching either flat stock or tubing. Preferably materials include nitinol, spring temper stainless steel and the like.

Figure 12A:
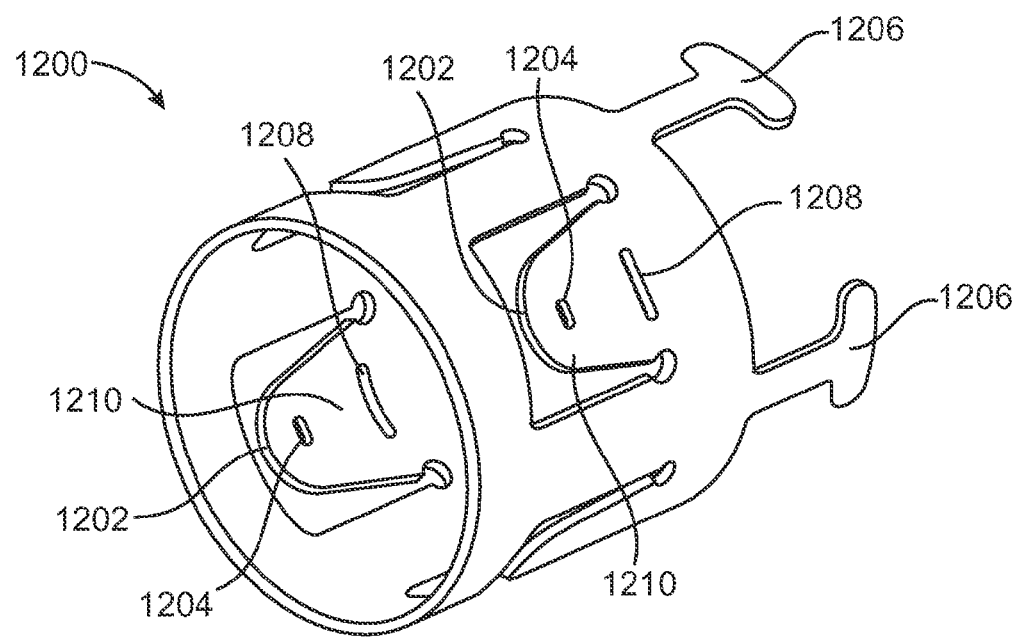
FIGS. 12A and 12B show a perspective and an unrolled, flattened view of another exemplary embodiment of a stent valve.
Figure 12B:
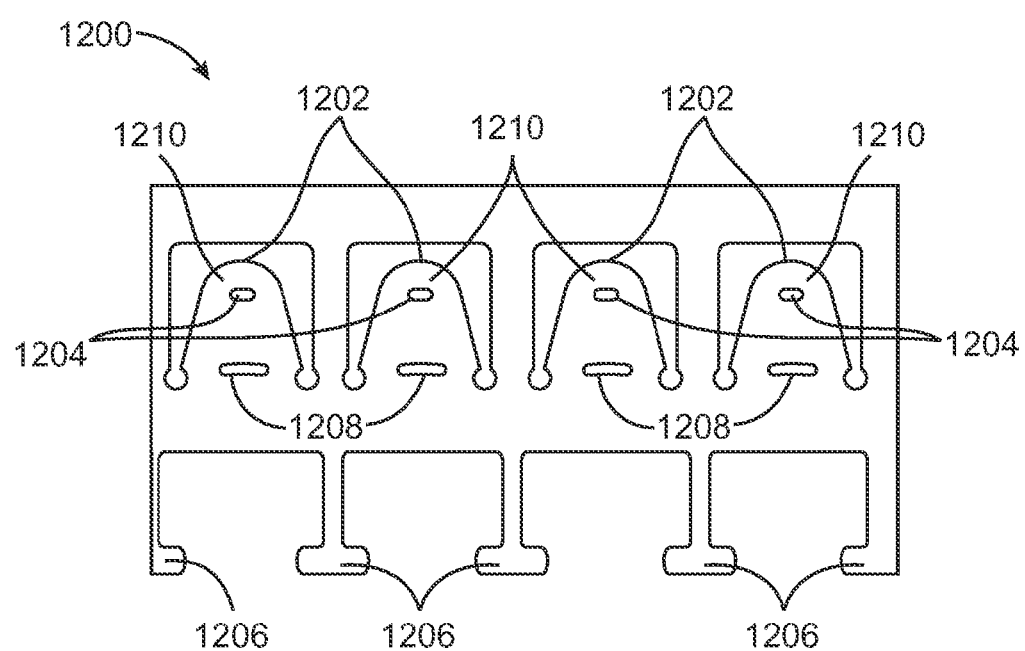

FIGS. 12A and 12B show still another embodiment of a stent valve. In FIG. 12A, stent valve 1200 includes a one-way grip structure or tab 1210 having an arcuate, resilient tip 1202 or finger in accordance with an embodiment. The stent valve 1200 may be embedded in the outer sheath or attached to its distal end. Stent valve 1200 has four tabs 1210 spaced approximately 90° apart. Each tab 1200 has a radiused end 1202 designed to facilitate engagement with a stent segment end when the valve 1200 is moved in the distal direction. Additionally, each tab has a hinge section 1204 where the tab may be bent inward to further enhance engagement with a stent segment. A hinge section 1208 allows the tab 1210 to flex as the stent valve is moved proximally and distally over the stent segments. Attachment tabs 1206 allow the stent valve 1200 to be attached with the distal end of an outer sheath. Fabrication of the stent valve 1200 is preferably by laser cutting, EDM machining or photoetching either a flat sheet or tube of nitinol, spring temper stainless steel and the like.

Figure 13:
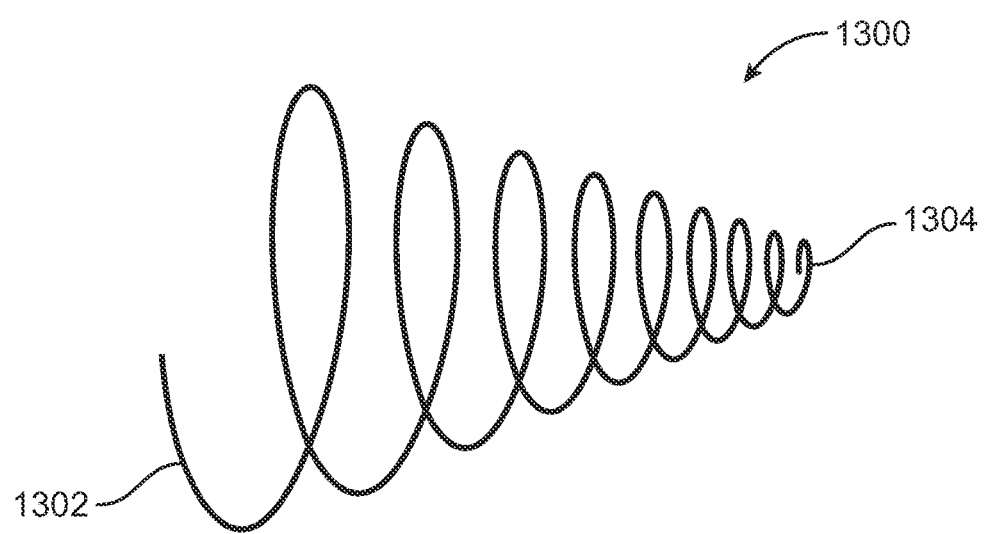
FIG. 13 illustrates another stent valve embodiment.

FIG. 13 illustrates another stent valve embodiment. In FIG. 13, stent valve 1300 is a spiral, conically shaped spring coil formed from wire or a polymer having a proximal end 1302 of larger diameter than the distal end 1304. The proximal end may be attached with the distal end of an outer sheath or the proximal end may be coupled with the inner surface of an outer sheath. During stent segment selection, stent valve 1300 is retracted proximally with a sheath. The spring coil unwinds and therefore the stent valve 1300 will slide over the stent segments. After the number of stent segments has been selected, the stent valve 1300 is advanced distally in order to separate the selected segments from those remaining with the delivery catheter. As stent valve 1300 is advanced distally the spring coil will compress until it forms a pusher that can advance stent segments distally.

In all embodiments of stent valves, the valves are adapted to slide over the prosthetic segments without damaging or removing any drug coatings on the surfaces of the segments.

While the exemplary embodiments have been described in some detail for clarity of understanding and by way of example, a variety of additional modifications, adaptations and changes may be clear to those of skill in the art. Hence, the scope of the present invention is limited solely by the appended claims.

What is claimed is:

1. An apparatus for delivering prosthetic segments in a body lumen, the apparatus comprising:
   an elongated flexible member having a proximal end and a distal end;
   a plurality of prosthetic segments releasably arranged axially along the elongated flexible member near the distal end;
   an outer sheath slidably disposed over at least a portion of the prosthetic segments;
   an inwardly extending separator fixedly attached to an inside surface of the outer sheath and positioned proximally from a distal end thereof, the inwardly extending separator being adapted to engage the prosthetic segments, wherein the inwardly extending separator is adapted to be refracted proximally to slide over the prosthetic segments and advanced distally to engage at least one prosthetic segment within the outer sheath and separate a proximal group of the prosthetic segments from a distal group of the prosthetic segments which are to be deployed in the body lumen.

2. An apparatus as in claim 1, further comprising a backstop element disposed on the elongated flexible member and adapted to prevent proximal movement of the prosthetic segments when the separator is retracted proximally over the prosthetic segments.

3. An apparatus as in claim 2, wherein the backstop element is a tube slidably disposed on the elongated flexible member.

4. An apparatus as in claim 2, wherein the backstop element is an annular flange disposed on the elongated flexible member.

5. An apparatus as in claim 2, wherein the backstop element is a balloon.

6. An apparatus as in claim 2, wherein the backstop element comprises a compliant spacer.

7. An apparatus as in claim 1, further comprising a stopping member disposed on the distal end of the elongated flexible member and adapted to stop distal movement of the prosthetic segments when the separator is advanced distally with the prosthetic segments.

8. The apparatus as in claim 7, further comprising a nosecone disposed at the distal end of the elongated flexible member, the nosecone being positioned distally of the stopping member and having a radial dimension that is greater than a radial dimension of the stopping member.

9. An apparatus as in claim 1, wherein the prosthetic segments are balloon expandable.

10. An apparatus as in claim 1, wherein the prosthetic segments are self-expanding.

11. An apparatus as in claim 1, further comprising an expandable member near the distal end of the elongated flexible member.

12. An apparatus as in claim 11, wherein the expandable member is a balloon.

13. An apparatus as in claim 1, wherein the plurality of prosthetic segments carry a therapeutic agent adapted to being released therefrom.

14. An apparatus as in claim 13, wherein the therapeutic agent comprises an anti-restenosis agent.

15. An apparatus as in claim 1, wherein the plurality of prosthetic segments have a length in the range from about 2 mm to about 10 mm.

16. An apparatus as in claim 1, wherein the plurality of prosthetic segments have a length about 3 mm to 6 mm.

17. An apparatus as in claim 1, wherein the plurality of prosthetic segments have interleaved ends prior to deployment.

18. An apparatus as in claim 1, wherein ends of the plurality of prosthetic segments are spaced apart prior to deployment to allow the separator to engage the prosthetic segments at their proximal ends.

19. An apparatus as in claim 1, wherein the plurality of prosthetic segments are initially spaced proximally from the distal end of the elongate flexible member to allow the distal group of prosthetic segments to be advanced distally by the separator.

20. An apparatus as in claim 1, wherein the separator exerts substantially greater axial force against the prosthetic segments when the separator is advanced distally than when the separator is retracted proximally.

21. An apparatus as in claim 1, wherein the separator comprises a plurality of resilient fingers projecting radially inward.

22. An apparatus as in claim 21, wherein at least some of the fingers are inclined so that free ends of the fingers point distally allowing the fingers to pass over the prosthetic segments as the separator is retracted proximally but to engage a prosthetic segment when the separator is advanced distally.

23. An apparatus as in claim 22, wherein at least some of the fingers are composed of metal.

24. An apparatus as in claim 22, wherein at least some of the fingers are composed of a polymer.

25. An apparatus as in claim 22, wherein at least some of the fingers comprise a radiused end substantially matching the curvature of the surface of the prosthetic segment thereby providing greater contact surface so as to facilitate engagement between the prosthetic segments and the separator as the separator is advanced distally while allowing the separator to pass over the prosthetic segments during proximal retraction of the separator.

26. An apparatus as in claim 22, wherein the separator further comprises a hinge coupled to the resilient fingers to allow the resilient fingers to deflect radially to facilitate passage of the separator over the prosthetic segments when the separator is retracted proximally.

27. An apparatus as in claim 1, wherein the separator comprises an annular flange.

28. An apparatus as in claim 27, wherein the annular flange is tapered.

* * * * *